(12) United States Patent
Noseworthy et al.

(10) Patent No.: US 11,337,637 B2
(45) Date of Patent: May 24, 2022

(54) ELECTROCARDIOGRAM ANALYTICAL TOOL

(71) Applicant: Mayo Foundation for Medical Education and Research, Rochester, MN (US)

(72) Inventors: Peter A. Noseworthy, Rochester, MN (US); Bo Qiang, Rochester, MN (US); Paul A. Friedman, Rochester, MN (US); Alan M. Sugrue, Rochester, MN (US); Vaclav Kremen, Rochester, MN (US); Bryan L. Striemer, Zumbrota, MN (US); Charles J. Bruce, Ponte Verda, FL (US); Virend K. Somers, Rochester, MN (US); Kevin E. Bennet, Rochester, MN (US); Michael J. Ackerman, Rochester, MN (US); Samuel J. Asirvatham, Rochester, MN (US); John J. Dillon, Rochester, MN (US); Christopher V. DeSimone, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 80 days.

(21) Appl. No.: 16/329,480

(22) PCT Filed: Aug. 31, 2017

(86) PCT No.: PCT/US2017/049568
§ 371 (c)(1),
(2) Date: Feb. 28, 2019

(87) PCT Pub. No.: WO2018/045147
PCT Pub. Date: Mar. 8, 2018

(65) Prior Publication Data
US 2021/0275080 A1  Sep. 9, 2021

Related U.S. Application Data

(60) Provisional application No. 62/382,082, filed on Aug. 31, 2016.

(51) Int. Cl.
*A61B 5/364* (2021.01)
*G16H 50/30* (2018.01)
(Continued)

(52) U.S. Cl.
CPC .............. *A61B 5/364* (2021.01); *A61B 5/339* (2021.01); *A61B 5/353* (2021.01); *A61B 5/355* (2021.01);
(Continued)

(58) Field of Classification Search
CPC ......... A61B 5/364; A61B 5/355; A61B 5/353; A61B 5/339; A61B 5/366; A61B 5/7203; G16H 50/30; G16H 50/20
See application file for complete search history.

(56) References Cited

U.S. PATENT DOCUMENTS 7,623,910 B2   11/2009   Courdec et al.
7,991,458 B2   8/2011    Hardahl et al.
(Continued)

FOREIGN PATENT DOCUMENTS

WO   WO 2015/048514       4/2015
WO   WO 2016/035000   *   3/2016

OTHER PUBLICATIONS

Ackerman et al., "Epinephrine-induced qt interval prolongation: A gene-specific paradoxical response in congenital long qt syndrome<" Mayo Clin. Proc., 77(5):413-21, May 2002.
(Continued)

*Primary Examiner* — Catherine M Voorhees
*Assistant Examiner* — Roland Dinga
(74) *Attorney, Agent, or Firm* — Fish & Richardson P.C.

(57) ABSTRACT

Systems, methods, devices, and techniques for analyzing and applying features of a T-wave derived from an electrocardiogram. A computing system can receive a set of data that characterizes an electrocardiogram of a patient. The system can analyze the set of data to identify a T-wave that
(Continued)

occurs in the electrocardiogram. The system can determine values of one or more features of the T-wave and provide the information that identifies the values of the one or more features of the T-wave to a user.

22 Claims, 7 Drawing Sheets

(51) Int. Cl.
　　　G16H 50/20　　　(2018.01)
　　　A61B 5/355　　　(2021.01)
　　　A61B 5/353　　　(2021.01)
　　　A61B 5/339　　　(2021.01)
　　　A61B 5/366　　　(2021.01)
　　　A61B 5/00　　　　(2006.01)

(52) U.S. Cl.
　　　CPC ............ *A61B 5/366* (2021.01); *A61B 5/7203* (2013.01); *G16H 50/20* (2018.01); *G16H 50/30* (2018.01)

(56) References Cited

U.S. PATENT DOCUMENTS

| | | | |
|---|---|---|---|
| 2005/0222511 A1 | 10/2005 | Hadley et al. | |
| 2007/0208264 A1* | 9/2007 | Hardahl | A61B 5/349 600/510 |
| 2008/0033313 A1 | 2/2008 | Couderc et al. | |
| 2008/0188761 A1* | 8/2008 | Couderc | A61B 5/349 600/509 |
| 2010/0222690 A1* | 9/2010 | Shvilkin | A61B 5/349 600/515 |
| 2012/0179055 A1* | 7/2012 | Tamil | A61B 5/726 600/509 |
| 2016/0035000 A1 | 2/2016 | Xu | |
| 2016/0135705 A1 | 5/2016 | Liu et al. | |
| 2016/0256063 A1* | 9/2016 | Friedman | A61B 5/02455 |
| 2019/0246966 A1* | 8/2019 | Friedman | A61B 5/14546 |

OTHER PUBLICATIONS

Ackerman, "My approach to treatment of the congenital long qt syndromes," Trends Cardiovasc. Med., 25(1):67-9, Jan. 2015.
Antzelevitch and Shimizu, "Cellular mechanisms underlying the long QT syndrome," Curr. Opin. Cardiol., 17(1):43-51, Jan. 2002.
Benhorin et al., "Variable expression of long QT syndrome among gene carriers from families with five different HERG mutations," Ann. Noninvasive Electrocardiol., 7(1):40-6, Jan. 2001.
Chorin et al., "Diagnostic value of t-wave morphology changes during "qt stretching" in patients with long qt syndrome," Heart Rhythm, 12(11):2263-71, Nov. 2015.
Couderc et al., "Impaired T-amplitude adaptation to heart rate characterizes I(Kr) inhibition in the congenital and acquired forms of the long QT syndrome," J. Cardiovasc. Electrophysiol., 18(12):1299-305, Oct. 2007.
Couderc et al., "T-wave morphology abnormalities in benign, potent, and arrhythmogenic I(kr) inhibition," Heart Rhythm, 8(7):1036-43, Jul. 2011.
Dausse et al., "A mutation in herg associated with notched t waves in long qt syndrome," J. Mol. Cell Cardiol., 28(8): 1609-15, Aug. 1996.
Extended European Search Report in EP Appln. No. 17847536, 9 pages dated Jul. 18, 2019.
Goldenberg et al., "Corrected qt variability in serial electrocardiograms in long qt syndrome: The importance of the maximum corrected qt for risk stratification," J. Am. Coll. Cardiol., 48(5):1047-52, Sep. 2006.
Gonzalez et al., "A systematic review on the cost-effectiveness of genetic and electrocardiogram testing for long qt syndrome in infants and young adults," Value Health, 18(5):700-8, Jul. 2015.
Graff et al., "Identifying drug-induced repolarization abnormalities from distinct ECG patterns in congenital long QT syndrome: a study of sotalol effects on T-wave morphology," Drug Saf., 32(7):599-611, Jul. 2009.
Gupta et al., "T(p-e)/QT ratio as an index of arrhythmogenesis," J. Electrocardiol., 41(6):567-74, Nov. 2008.
Haarmark et al., "The prognostic value of the Tpeak-Tend interval in patients undergoing primary percutaneous coronary intervention for ST-segment elevation myocardial infarction," J. Electrocardiol., 42(6):555-60, Nov. 2009.
Haugaa et al., "Institution-wide QT alert system identifies patients with a high risk of mortality," Mayo Clin. Proc., 88(4):315-25, Apr. 2013.
Hondeghem, "Thorough QT/QTc not so thorough: removes torsadogenic predictors from the T-wave, incriminates safe drugs, and misses profibrillatory drugs," J. Cardiovasc. Electrophysiol., 17(3):337-40, Mar. 2006.
Kannankeril et al., "Drug-induced long QT syndrome," Pharmacol. Rev., 62(4):760-8, Dec. 2010.
Kanters et al., "T wave morphology analysis distinguishes between kvlqt1 and herg mutations in long qt syndrome," Heart Rhythm, 1(3):285-92, Sep. 2004.
Kapa et al., "Genetic testing for long-qt syndrome: Distinguishing pathogenic mutations from benign variants," Circulation, 120(18):1752-60, Oct. 2009.
Khositseth et al., "Epinephrine-induced t-wave notching in congenital long qt syndrome," Heart Rhythm, 2(2):141-6, Feb. 2005.
Lehmann et al., "T wave "humps" as a potential electrocardiographic marker of the long QT syndrome," J. Am. Coll. Cardiol., 24(3):746-54, Sep. 1994.
Lehtonen et al., "Further evidence of inherited long QT syndrome gene mutations in anti arrhythmic drug-associated torsades de pointes," Heart Rhythm 4(5):603-7, May 2007.
Letsas et al., "Tpeak-Tend interval and Tpeak-Tend/QT ratio as markers of ventricular tachycardia inducibility in subjects with Brugada ECG phenotype," Europace, 12(2):271-4, Feb. 2010.
Malfatto et al., "Quantitative analysis of t wave abnormalities and their prognostic implications in the idiopathic long qt syndrome," J. Am. Coll. Cardiol., 23(2):296-301, Feb. 1994.
Matsuda, "Magnesium gating of the inwardly rectifying K+ channel," Annu. Rev. Physiol., 53(1):289-98, Mar. 1991.
Moss et al., "ECG T-wave patterns in genetically distinct forms of the hereditary long QT syndrome," Circulation, 92(10):2929-34, Nov. 1995.
Numaguchi et al., "A sensitive mechanism for cation modulation of potassium current," Nat. Neurosci., 3(5):429-30, May 2000.
Pavriet et al., "T wave slopes: a novel method for assessment of repolarization dispersion from surface ECGS with prolonged AT as compared to normal ECGs," J. Am. Coll. Cardiol., 63(Suppl. 12):A1638, Apr. 2014.
PCT International Preliminary Report on Patentability Report in International Appln. No. PCT/US2017/049568 dated Mar. 14, 2019, 8 pages.
PCT International Search Report and Written Opinion in International Appln. No. PCT/US2017/049568 dated Nov. 16, 2017, 9 pages.
Perez et al., "Cost-effectiveness of genetic testing in family members of patients with long-qt syndrome," Circ. Cardiovasc. Qual. Outcomes, 4(1):76-84, Jan. 2011.
Priori et al., "HRS/EHRA/APHRS expert consensus statement on the diagnosis and management of patients with inherited primary arrhythmia syndromes," Heart Rhythm, 10(12): 1932-63, Dec. 2013.
Roden, "Drug-induced prolongation of the QT interval," N. Eng. J. Med., 350(10): 1013-22, Mar. 2004.
Rushing et al., "A leave-one-out cross-validation SAS macro for the identification of markers associated with survival," Comput. Biol. Med., 57:123-9, Feb. 2015.
Sara et al., "Electrocardiographic predictors of coronary microvascular dysfunction in patients with non-obstructive coronary artery disease: Utility of a novel T wave analysis program," 203:601-6, Nov. 2015.

(56) References Cited

OTHER PUBLICATIONS

Schwartz and Crotti., "Qtc behavior during exercise and genetic testing for the long-qt syndrome," Circulation, 124(20):2181-4, Nov. 2011.
Schwartz et al., "Genotype-phenotype correlation in the long-QT syndrome: genespecific triggers for life-threatening arrhythmias," Circulation, 03(1):89-95, Jan. 2001.
Schwartz et al., "Prevalence of the congenital long-QT syndrome." Circulation, 120(18):1761-7, Nov. 2009.
Shimizu et al., "T-peak to T-end interval may be a better predictor of high-risk patients with hypertrophic cardiomyopathy associated with a cardiac troponin I mutation than QT dispersion," Clin. Cardiol., 25(7):335-9, Jul. 2002.
Sugrue et al., "Electrocardiographic predictors of torsadogenic risk during dofetilide or sotalol initiation: utility of a novel T wave analysis program," Cardiovas. Drugs Ther., 29(5):433-41, Oct. 2015.
Sugrue et al., "Identification of Concealed and Manifest Long QT Syndrome Using a Novel T Wave Analysis Program," Circ. Arrhythm. Electrophysiol., 9(7):e003830, Jul. 2016.
Sugrue et al., "Identification of Genotype-specific Electrocardiogram Patterns in Long QT Syndrome Using a Novel, Automated T Wave Analysis Program," Circulation, 132(Suppl. 3):A17604, Nov. 2015.
Swan et al., "Sinus node function and ventricular repolarization during exercise stress test in long qt syndrome patients with kvlqt1 and herg potassium channel defects," J. Am. Coll. Cardiol., 34(3):823-9, Sep. 1999.
Sy et al., "Derivation and validation of a simple exercise-based algorithm for prediction of genetic testing in relatives of lqts probands," Circulation, 124(20):2187-94, Oct. 2011.
Takenaka et al., "Exercise stress test amplifies genotype-phenotype correlation in the lqt1 and lqt2 forms of the long-qt syndrome," Circulation, 107(6):838-44, Feb. 2003.
Tanabe et al., "Sympathetic stimulation produces a greater increase in both transmural and spatial dispersion of repolarization in lqt1 than lqt2 forms of congenital long qt syndrome," J. Am. Coll. Cardiol., 37(3):911-9, Mar. 2001.
Thomsen et al., "Beat-to-Beat variability of repolarization determines proarrhythmic outcome in dogs susceptible to drug-induced torsades de pointes," J. Am. Coll. Cardiol., 48(6):1268-76, Sep. 2006.
Topilski et al., "The morphology of the QT interval predicts torsade de pointes during acquired bradyarrhythmias," J. Am. Coll. Cardiol., 49(3):320-8, Jan. 2007.
Vandenberg, "Inward rectification of a potassium channel in cardiac ventricular cells depends on internal magnesium ions," Proc. Natl. Acad. Sci. USA, 84(8):2560-4, Apr. 1987.
Veerman et al., "Slow delayed rectifier potassium current blockade contributes importantly to drug-induced long QT syndrome," Circ. Arrhythm. Electrophysiol., 6(5): 1002-9, Oct. 2013.
Viitasalo et al., "Differentiation between lqt1 and lqt2 patients and unaffected subjects using 24-hour electrocardiographic recordings," Am. J. Cardiol., 89(6):679-85, Mar. 2002.
Vincent et al., "The spectrum of symptoms and qt intervals in carriers of the gene for the long-qt syndrome," N. Engl. J. Med., 327(12):846-52, Sep. 1992.
Viskin et al., "Provocation of sudden heart rate oscillation with adenosine exposes abnormal qt responses in patients with long qt syndrome: A bedside test for diagnosing long qt syndrome," Eur. Heart J., 27(4):469-75, Feb. 2006.
Viskin et al., "The response of the qt interval to the brief tachycardia provoked by standing: A bedside test for diagnosing long qt syndrome," J. Am. Coll. Cardiol., 55(18):1955-61, May 2010.
Vyas and Ackerman, "Epinephrine qt stress testing in congenital long qt syndrome," J. Electrocardiol., 39(4):S107-13, Oct. 2006.
Wilde and Bezzina, "Genetics of cardiac arrhythmias," Heart, 91(10):1352-8, Sep. 2005.
Wong et al., "Utility of treadmill testing in identification and genotype prediction in long-qt syndrome," Circ. Arrhythm. Electrophysiol., 3(2):120-125, Apr. 2010.
Yan and Antzelevitch, "Cellular basis for the normal T wave and the electrocardiographic manifestations of the long-QT syndrome," Circulation, 98(18):1928-36, Nov. 1998.
Yang and Roden, "Extracellular potassium modulation of drug block of IKr, Implications for torsade de pointes and reverse use-dependence," Circulation, 93(3):407-11, Feb. 1996.
Yang et al., "Allelic variants in long-QT disease genes in patients with drug-associated torsades de pointes," Circulation, 105(16): 1943-8, Apr. 2002.
Yang et al.. "Rapid inactivation determines the rectification and [K+]o dependence of the rapid component of the delayed rectifier K+ current in cardiac cells," Circ. Res., 80(6):782-9, Jun. 1997.
Yap and Camm,"Drug induced QT prolongation and torsades de pointes," Heart, 89(11):1363-72, Nov. 2003.
Zareba, "Challenges of diagnosing long qt syndrome in patients with nondiagnostic resting qtc," J. Am. Coll. Cardiol., 55(18):1962-4, May 2010.
Zhang et al., "Spectrum of ST-T-wave patterns and repolarization parameters in congenital long-QT syndrome: ECG findings identify genotypes," Circulation, 102(23):2849-55, Dec. 2000.

\* cited by examiner

Table 2. The Top 3 Selected Features and Classification Success in Each of the ECG's 12 Leads

| Lead | Top Selected Features | | | Successful Classification % | |
|---|---|---|---|---|---|
| | 1 | 2 | 3 | LQT Cohort | Concealed Asymptomatic Cohort |
| I | Last 25% of T wave COG x axis | Left slope T wave | T peak–T end interval | 87.12 | 79.76 |
| II | Last 25% of T wave COG x axis | Left slope T wave | T wave amplitude | 86.48 | 77.38 |
| III | Last 25% of T wave COG x axis | COG y axis | | 54.29 | 75.00 |
| aVR | Last 25% of T wave COG x axis | Left slope T wave | T peak–T end interval | 89.27 | 78.57 |
| aVL | Last 25% of T wave COG x axis | T wave area | | 89.91 | 82.35 |
| aVF | Last 25% of T wave COG x axis | Left slope T wave | | 89.06 | 81.48 |
| V1 | T wave COG x axis | Last 25% of T wave COG y axis | | 78.97 | 70.59 |
| V2 | T wave COG x axis | Right slope T wave | | 83.77 | 75.00 |
| V3 | Last 25% of T wave COG x axis | Last 25% of T wave COG y axis | T peak–T end interval | 86.41 | 77.78 |
| V4 | Last 25% of T wave COG x axis | Last 25% of T wave COG y axis | T peak–T end interval | 87.77 | 78.75 |
| V5 | Last 25% of T wave COG x axis | Last 25% of T wave COG y axis | T peak–T end interval | 86.48 | 80.95 |
| V6 | Last 25% of T wave COG x axis | Left slope T wave | T peak–T end interval | 86.8 | 83.33 |

Lead V6 is given in bold to highlight the lead we selected for analysis. COG indicates center of gravity, and LQT, long QT.

FIG. 4

Table – Baseline characteristics of study cohort.

| | Congenital LQTS | Acquired QT Prolongation |
|---|---|---|
| Number | 38 | 114 |
| Male, n (%) | 8 (25%) | 45 (47%) |
| Age, years ± SD | 15 ± 12 | 66 ± 14 |
| QTc, msec ± SD | 499 ± 30 | 520 ± 29 |
| Etiology (%) | | |
| Drugs | | 78 (81%) |
| Hypocalcemia | | 33 (34%) |
| Hypokalemia | | 25 (26%) |
| Hypomagnesemia | | 25 (26%) |

LQTS – long QT syndrome. QTc, heart rate-corrected QT interval by Bazett formula

FIG. 6

ELECTROCARDIOGRAM ANALYTICAL TOOL

CROSS REFERENCE TO RELATED APPLICATIONS

This application is a National Stage application under 35 U.S.C. § 371 of International Application No. PCT/US2017/049568, having an International Filing Date of Aug. 31, 2017, which claims the benefit of priority to U.S. Provisional Application Ser. No. 62/382,082, filed Aug. 31, 2016. The disclosures of the prior applications are considered part of (and are incorporated by reference in) the disclosure of this application.

TECHNICAL FIELD

This document generally describes computer-based technology for analyzing physiological electrical data (e.g., electrocardiogram data).

BACKGROUND

Electrocardiograms are commonly used to assess the electrical activity of a patient's heart. The tracing of an electrocardiogram can show a patient's typical sinus rhythm and may include various segments that represent different portions of the sinus rhythm for each beat. For example, different segments may correspond to each of a P-wave, a QRS-complex, and a T-wave. Because a number of physiological conditions of a patient may impact the electrical activity of a patient's heart, studies have linked characteristics of a patient's electrocardiogram to various conditions. Some conditions, however, may be linked to very subtle features of the electrocardiogram that cannot be detected by the naked eye or by conventional electrocardiogram equipment.

Long QT syndrome (LQTS) is a leading cause of sudden cardiac death (SCD) in the young. See Schwartz P J, Stramba-Badiale M, Crotti L, et al. Prevalence of the congenital long-QT syndrome. *Circulation* 2009; 120(18):1761-7. doi: 10.1161/CIRCULATIONAHA.109.863209. Patients with LQTS have abnormal or delayed ventricular repolarization that often manifests itself as a prolonged QT interval on the surface electrocardiogram (ECG). This abnormality of repolarization predisposes to life-threatening cardiac events (CEs). While it is established that life-threatening arrhythmias often occur under specific circumstances in a gene-specific manner (see Schwartz P J, Priori S G, Spazzolini C, et al. Genotype-phenotype correlation in the long-QT syndrome: gene-specific triggers for life-threatening arrhythmias. *Circulation* 2001; 103(1):89-95), the ability to identify those at highest phenotypic risk of CEs remains poor, particularly in those at risk of continued arrhythmic events while being treated intentionally for their underlying LQTS substrate. See Benhorin J, Moss A J, Bak M, et al. Variable expression of long QT syndrome among gene carriers from families with five different HERG mutations. *Ann Noninvasive Electrocardiol* 2002; 7(1):40-6.

SUMMARY

This specification discloses computer-based systems, methods, devices, and other techniques for processing, visualizing, and analyzing electrocardiogram data. In some implementations, one or more computers may provide an ECG analytical tool that can automatically classify segments of an ECG signal, determine values of features associated with one or more of the segments, and display an interface that represents the ECG signal and corresponding features.

Some implementations of the techniques described herein include a computer-implemented method. The method includes receiving, by a computing system, a set of data that characterizes an electrocardiogram of a patient. The computing system analyzes the set of data that characterizes the electrocardiogram of the patient to identify a T-wave that occurs in the electrocardiogram, and determines values of one or more features of the T-wave, e.g., in response to automatically identifying the T-wave. The computing system can then provide to a client device of a user information that identifies the values of the one or more features of the T-wave. The computing system may also determine, based on the values for the one or more features of the T-wave, whether the patient has or is at risk of having one or more cardiac conditions.

These and other implementations can optionally include one or more of the following features.

The computing system, the client device, or both can activate one or more alerts when particular combinations of one or more of the features of the T-wave fall above or below pre-defined limits, e.g., to provide feedback to a healthcare professional or a patient of one or more conditions associated with the particular combinations of T-wave features. In some implementations, an alert or other indication is presented (e.g., displayed on a screen of a computing system or device) that indicates one or more cardiac conditions the patient is determined to have or is determined to be susceptible to based on analysis of the values of the T-wave features.

The computing system, the client device, or both can generate signals that cause automatic adjustment of therapeutic parameters for ongoing therapy being administered to a patient or for therapy that is planned to be administered to the patient at a future time.

Analyzing the set of data that characterizes the electrocardiogram of the patient can include automatically identifying a particular segment of the electrocardiogram that corresponds to the T-wave, from among a plurality of segments of the electrocardiogram that correspond to different portions of the electrocardiogram. The different portions of the electrocardiogram can include the T-wave and at least one of a P-wave or a QRS-complex.

The computing system can display, in a graphical user interface on an electronic display coupled to the computing system, a visual representation of the electrocardiogram for one or more heartbeats of the patient. In conjunction with displaying the visual representation of the electrocardiogram, the computing system can visually mark the particular segment of the electrocardiogram that corresponds to the T-wave.

In conjunction with displaying the visual representation of the electrocardiogram, the computing system can visually mark a second segment of the electrocardiogram that corresponds to the QRS-complex.

While displaying the visual representation of the electrocardiogram, the computing system can provide a control in the graphical user interface that allows a user to confirm or reject the particular segment of the electrocardiogram that the computing system automatically identified as corresponding to the T-wave of the patient's heartbeat. The computing system can receive input that indicates user selection of the control and a confirmation or rejection of the particular segment of the electrocardiogram as corresponding to the true T-wave of the patient's heartbeat.

The computing system can adjust a boundary of the particular segment of the electrocardiogram that corresponds to the T-wave of the patient's heartbeat according to user input that specifies the adjustment.

Raw data can be received that characterizes the electrocardiogram of the patient. The raw data can be processed to generate modified data that characterizes the electrocardiogram of the patient. The computing system can perform at least one of the analyzing step or the determining step with respect to the modified data.

The raw data that characterizes the electrocardiogram of the patient can include at least one of removing noise from the electrocardiogram or removing baseline wander from the electrocardiogram.

Processing the raw data that characterizes the electrocardiogram of the patient can include using a signal averaging technique to determine a representative beat of the electrocardiogram based on data that characterizes multiple beats of the patient.

Processing the raw data that characterizes the electrocardiogram of the patient can include identifying one or more beats that are deemed outliers from one or more other beats represented in the electrocardiogram, and generating a representative beat of the electrocardiogram based on data that characterizes a plurality of beats represented in the electrocardiogram to the exclusion of the one or more beats that are deemed outliers. The computing system performs at least one of the analyzing step or the determining step with respect to data that characterizes the representative beat.

Processing the raw data that characterizes the electrocardiogram of the patient can include identifying data recorded from one or more leads of a multi-lead electrocardiogram device, and removing the data recorded from the one or more leads of the multi-lead electrocardiogram device. The computing system can perform at least one of the analyzing step or the determining step based on a portion of data received by the computing system that excludes the data recorded from the one or more leads of the multi-lead electrocardiogram device.

The one or more features of the T-wave can include at least one of T-wave left slope, T-wave right slope, T-wave area, T-wave amplitude, time interval of t-peak to t-end, T-wave center-of gravity, x/y coordinates of the center of gravity (COG) of the first 25% of a T-wave (T1), x/y coordinates of COG of the last 25% of a T-wave (T4), QT interval, or QTc value The computing system can determine respective values of the one or more-features of the T-wave for a population of patients. Statistical analysis of the respective values of the one or more features of the T-wave can be performed for the population of patients. Based on a result of the statistical analysis, values of at least one feature of the T-wave can be correlated with a patient condition.

The patient condition can be a cardiac disease, e.g., long-QT syndrome, Torsades de pointes, or Coronary Microvascular Dysfunction.

Based on the result of the statistical analysis, the computing system can correlate first values of at least one feature of the T-wave with congenital long-QT syndrome. Based on the result of the statistical analysis, the computing system can correlate second values of at least one feature of the T-wave with acquired long-QT syndrome.

Some implementations of the subject matter described herein can include a computing system. The system can include one or more processors and one or more computer-readable media having instructions stored thereon that, when executed by the one or more processors, cause performance of operations. The operations can include receiving, by the computing system, a set of data that characterizes an electrocardiogram of a patient; analyzing, by the computing system, the set of data that characterizes the electrocardiogram of the patient to identify a T-wave that occurs in the electrocardiogram; determining, by the computing system and in response to identifying a T-wave that occurs in the electrocardiogram, values of one or more features of the T-wave; and providing, by the computing system and to a client device of a user, information that identifies the values of the one or more features of the T-wave, or information derived from the values of the one or more features of the T-wave that characterize the patient as having or being at risk of a cardiac condition.

Some implementations of the subject matter described herein include one or more non-transitory computer-readable media. The media can have instructions stored thereon that, when executed by one or more processors, cause performance of operations, which include receiving, by a computing system, a set of data that characterizes an electrocardiogram of a patient; analyzing, by the computing system, the set of data that characterizes the electrocardiogram of the patient to identify a T-wave that occurs in the electrocardiogram; determining, by the computing system and in response to identifying a T-wave that occurs in the electrocardiogram, values of one or more features of the T-wave; and providing, by the computing system and to a client device of a user, information that identifies the values of the one or more features of the T-wave.

Some implementations of the subject matter disclosed here include a method, which can be a computer-implemented method. The method includes receiving, by a computing system, a set of data that characterizes an electrocardiogram of a patient. The system determines a representative beat (e.g., cardiac/heart beat) from the set of data that characterizes the electrocardiogram of the patient. The representative beat can be extracted as an individual beat from multiple beats recorded in the electrocardiogram, or the representative beat may be averaged from multiple beats. A T-wave that occurs in the representative beat is identified, and the system determines values for at least one of (i) a left slope feature of the T-wave in lead V6 of the electrocardiogram or (ii) a T-wave center-of-gravity in an x-axis of the electrocardiogram for a portion of the T-wave in lead I. The system determines whether the values for the at least one of the left slope feature of the T-wave in lead V6 or the T-wave center-of-gravity in the x-axis of the electrocardiogram for the portion of the T-wave satisfy one or more criteria (e.g., whether the left slope feature and/or the center-of-gravity in the x-axis meet pre-defined threshold value(s) for slope and/or center-of-gravity). In response to determining that the values for the at least one of the left slope feature of the T-wave in lead V6 or the T-wave center-of-gravity in the x-axis of the electrocardiogram for the portion of the T-wave satisfy the one or more criteria, the system can classify the patient as being at risk of future long-QT syndrome (LQTS)-associated cardiac events. Some implementations include one or more non-transitory computer-readable media having instructions stored thereon that, when executed by one or more processors, cause the one or more processors to perform the foregoing method. Some implementations include a computing system that includes the one or more processors in addition to the computer-readable media.

These and other implementations can optionally include one or more of the following features.

The representative beat can be a portion of the electrocardiogram for a complete beat or a portion of a beat in the electrocardiogram that includes a T-wave.

The x-axis can be a time axis of a plot of the electrocardiogram.

The portion of the T-wave can be a last 25-percent of the T-wave.

The method can further include generating an alert if the patient is classified as being at risk of future LQTS-associated cardiac events. Generating the alert can include at least one of transmitting a message indicating the patient is classified as being at risk of future LQTS-associated cardiac events, presenting a visual notification of the classification, or presenting an aural notification of the classification A healthcare professional can treat the patient based on the patient being classified as being at risk of future LQTS-associated cardiac events.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 depicts a table from an example study showing, for each lead of a 12-lead ECG, the top 3 selected T-wave features and classification success given those features.

FIG. 6 is a table representing baseline characteristics of a patient cohort in an example study.

Like references and indicators among the drawings indicate like elements.

DETAILED DESCRIPTION

Figure 1:
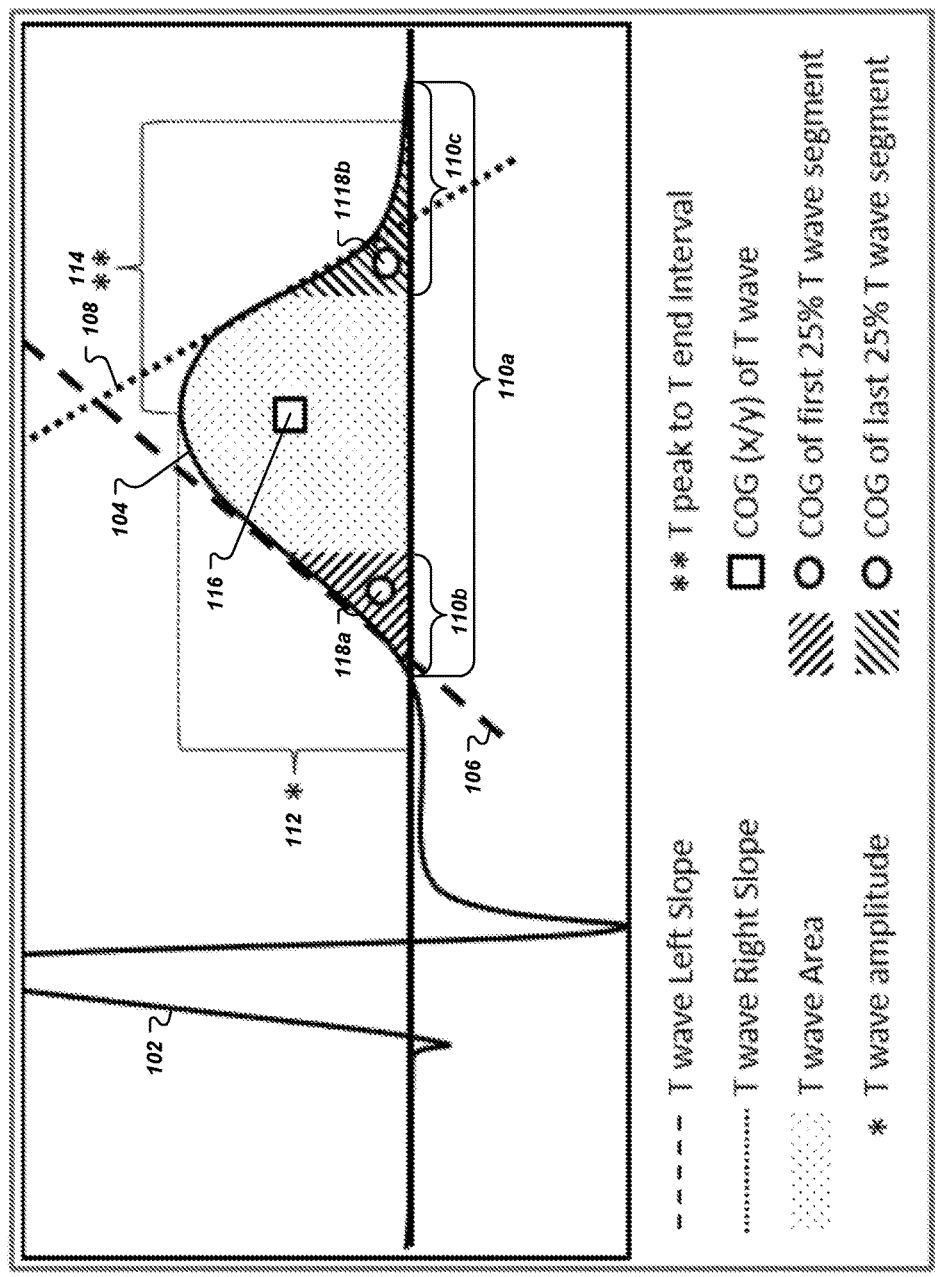
FIG. 1 is a diagram of an example ECG tracing, including markings for various features of the ECG that an analytical tool may determine according to some implementations. The diagram may be presented in a user interface for presentation to a user.

This specification discloses computer-based systems, methods, devices, and other techniques for analyzing and determining characteristics of electrocardiogram ("ECG") signals. Healthcare professionals have long administered ECGs to patients to evaluate patients' heart rhythm and to detect underlying cardiac disorders. Visual inspection of ECGs, whether recorded by analog or digital means, has facilitated the identification of various diseases and other patient conditions, such as dysrhythmias, heart murmurs, and possible myocardial infarction. More recently, research has shown that various characteristics (e.g., features) of a patient's ECG sometimes provide strong indicators of a range of additional patient conditions that were not conventionally evaluated using ECG data. By way of example, it has been shown elsewhere that concentrations of analytes (e.g., potassium) in a patient's bloodstream can be estimated by analysis of the patient's ECG. Electrocardiograms can thus provide an effective, non-invasive solution for identification and evaluation of patient conditions that have been correlated with one or more characteristics of an ECG signal.

Some implementations of the subject matter disclosed herein relate to a computer-based ECG analytical tool that facilitates the identification, evaluation, and presentation of features of a patient's ECG. In some implementations, the analytical tool may identify and evaluate very subtle ECG features that would not be capable of determination by visual inspection or by various other conventional techniques. Features such as these may nonetheless be correlated with patient conditions of interest, and hence the tool discussed herein may facilitate the work of researchers to identify new links between these subtle ECG features and new patient conditions. For instance, as discussed in the 'Example Implementation' section below, one example of a computer-based ECG analytical tool is used to discern ECG features that can help predict the occurrence of congenital long-QT syndrome versus acquired long-QT syndrome.

The analytical tool discussed herein is generally capable of processing ECG data, which is a form of physiological electrical data. Physiological electrical data may be obtained using any suitable technique such as electrocardiogram ("ECG") measurements (which may include surface, intracardiac, or subcutaneous ECGs, or measurements obtained using a pacemaker implanted in a patient's body, or defibrillators, for example). Either or both tonic or resting electrocardiograms may be employed, as well as ECGs that measure responses to provocations such as evoked stimuli or extrinsic electrical stimulation or other stimulation.

In the context of this document, ECG data generally refers to a recording of the electrical activity of a mammal's cardiovascular activity (e.g. heartbeat of a patient or other human). The ECG data may be recorded from a traditional surface ECG electrode, custom body surface electrodes that may vary in size, shape, and/or inter-electrode distance, for example, and/or from intracoporeal electrodes, whether they be subcutaneous, intracardiac, or within other tissues or natural cavities. ECGs from which such data is obtained may be spontaneous, or in response to a stimulus or provocation, and may be recorded from contact or non-contact electrodes. In some examples, electrogram data may be obtained from one or more of a standard 12 lead ECG, a wearable patch with one or more channels, and wearable elements including shirts, watches, bands and bracelets with conductive elements capable of recording physiologic signals. ECG data may be obtained in some examples from implanted devices such as loop recorders, pacemakers, and/or defibrillators.

While the term "computer-based" is applied, it is recognized that this may refer to any suitable form of computer processing, including mobile-based processing. For example, the techniques disclosed herein may be implemented at least in part by a mobile computing device such as a smartphone, tablet, or notebook computer that communicates with a system of wearable or hand-held electrodes. These techniques may also be implemented in wearable ECG patches or implantable devices. These techniques permit data compression and distribution of processing among various aspects of such a system, to enable near real-time, frequent, assessment of ECG features in ambulatory/outpatient individuals. Additionally, this paper broadly uses the term "patient" to generally include any person from whom ECG data is obtained, regardless of their clinical status for example.

Turning to FIG. 1, a diagram is shown of an example ECG tracing 100, including markings for various features of the ECG that an analytical tool may determine according to so some implementations of the techniques discussed herein. The ECG tracing 100 in this example is zoomed-in to show the electrical activity of a patient for a portion of one heartbeat. The segment 102 of the ECG tracing 100 on the left-hand side of the plot represents the QRS-complex of a patient, which includes a Q-wave that falls below the baseline (reference) voltage, an R-wave that follows the Q-wave and quickly shoots above the baseline voltage, and an S-wave that follows the Q-wave and again falls below the baseline voltage. Following the QRS-complex 102, the tracing shows the occurrence of a T-wave 104. By way of example, the features discussed herein relate specifically to features of the T-wave 104.

FIG. 1 shows eight features that a computing system implementing an ECG analytical tool may automatically compute based on data that specifies a given T-wave. These features are discussed individually in the following paragraphs. The analytical tool may generally be implemented on one or more computers in one or more locations.

In some implementations, the analytical tool may determine the value of the T-wave left-slope feature, which is represented in FIG. 1 by the dashed line element 106.

In some implementations, the analytical tool may determine the value of the T-wave right-slope feature, which is represented in FIG. 1 by the dotted line element 108.

In some implementations, the analytical tool may determine the value of the T-wave area, which is represented in FIG. 1 by the area bounded by the T-wave and the reference voltage (e.g., x-axis) and spanning a time interval 110a from a start of the T-wave to an end of the T-wave.

In some implementations, the analytical tool may determine the value of the T-peak to T-end interval 114, which indicates the amount of time between the peak amplitude of the T-wave and the end of the T-wave.

In some implementations, the analytical tool may determine the value of a center-of-gravity (COG) feature of the T-wave. The analytical tool may, for example, be configured compute the COG 116 of an entirety or substantial entirety of the T-wave 104 in the x-axis, the y-axis, or both, such as during the time interval 110a. In some instances, the analytical tool may further be configured to compute the COG 118a of a first quarter 110b of the T-wave 104 (in the x-axis, y-axis, or both), the COG 118b of a last quarter 110c of the T-wave 104 (in the x-axis, y-axis, or both), or the COGs 118a, 118b of both the first and last quarters 110b, 110c. Given a set of discrete (e.g., sampled) values of the ECG signal that define an entirety or a portion of the T-wave for which the COG is to be determined, the center-of-gravity may be determined as follows:

$$C_x = \frac{1}{6A} \sum_{i=0}^{n-1} (x_i + x_{i+1})(x_i y_{i+1} - x_{i+1} y_i)$$

$$C_y = \frac{1}{6A} \sum_{i=0}^{n-1} (y_i + y_{i+1})(x_i y_{i+1} - x_{i+1} y_i)$$

$$A = \frac{1}{2} \sum_{i=0}^{n-1} (x_i y_{i+1} - x_{i+1} y_i)$$

where $(C_x, C_y)$ are the x and y coordinates of the center of gravity, respectively. $(x_i, y_i)$ are the x and y coordinates of the ith point, respectively.

Each of the foregoing T-wave features characterizes an aspect of the T-wave, but some may be impractical to determine by conventional means, e.g., in a clinical setting. The analytical tool disclosed herein can thus facilitate the determination of these values, which may vary only subtly between patients, but can have significant impact on the determination of a patient's condition.

In some implementations, a computing system implementing an ECG analytical tool may provide a graphical user interface that displays information about a patient's ECG to a user. The user interface may show a plot or tracing of an ECG signal for a portion of a heartbeat or one or more complete heartbeats. The tool may also provide graphical markings over the plot or tracing of the ECG signal that visually indicate particular segments or features of the ECG signal. For example, the user interface may highlight or annotate segments such as the P-wave, QRS-complex, or T-wave. In some instances, graphical elements may be overlaid on a plot or tracing of an ECG to represent features, such as lines tangential to the left- or right-slopes of the T-wave from which the T-wave left- or right-slope features are calculated, respectively. The values of features determined by the computing system may also be presented within the user interface.

In some implementations, graphical elements representing particular features of the ECG wave may be user-selectable elements. A user may use a mouse, touchscreen gestures, or other pointing object to select an element and move the element within the user interface to make adjustments to the value of the feature that corresponds to the graphical element. For example, the computing system may process ECG data and automatically make an initial identification of the T-wave and values of various features of the T-wave. The system may present in the user interface a tangential line along the rising slope of the T-wave as a graphical element having a slope that corresponds to the determined T-wave left slope value. If a user desires to adjust the T-wave left slope value, for example, the displayed tangential line can be selected and dragged along the contour of the T-wave to a desired location specified by the user, and the slope of the line may update to reflect the instantaneous slope of the T-wave at the chosen location. In this way, the analytical tool may determine initial values of T-wave features, but the program provides the flexibility for users to refine the initially determined values.

Figure 2:
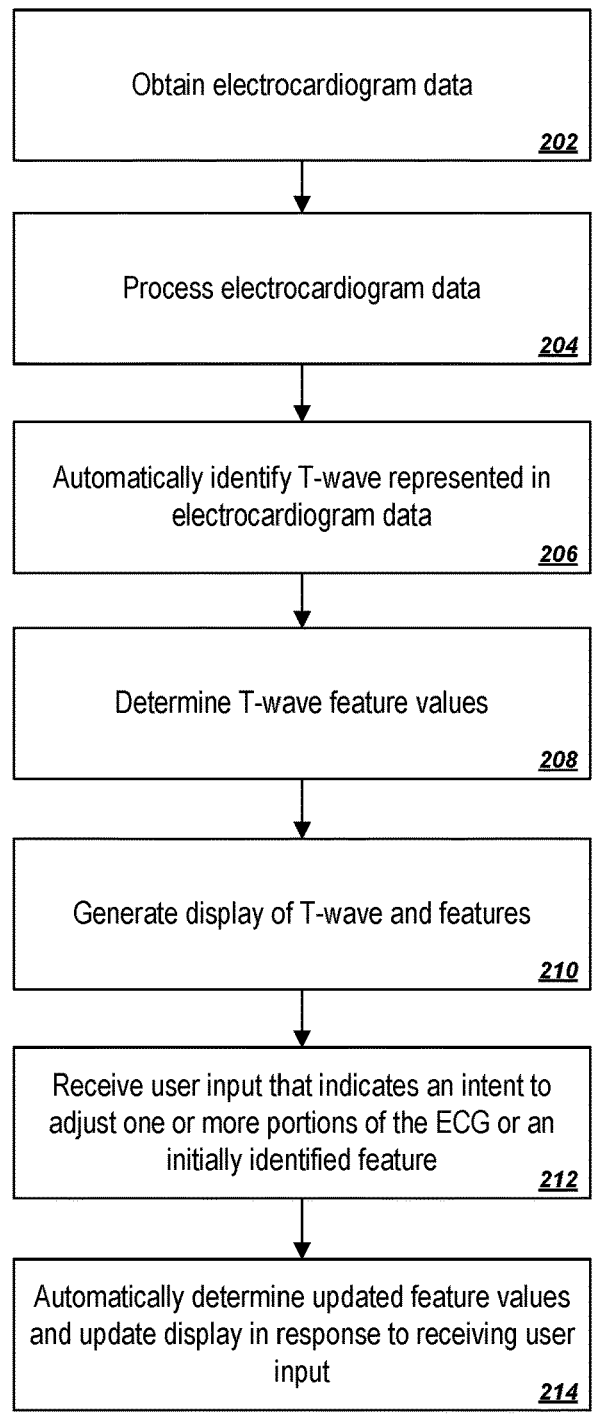
FIG. 2 is a flowchart of an example process for processing and visualizing ECG data with a computer-based ECG analytical tool.
Figure 3:
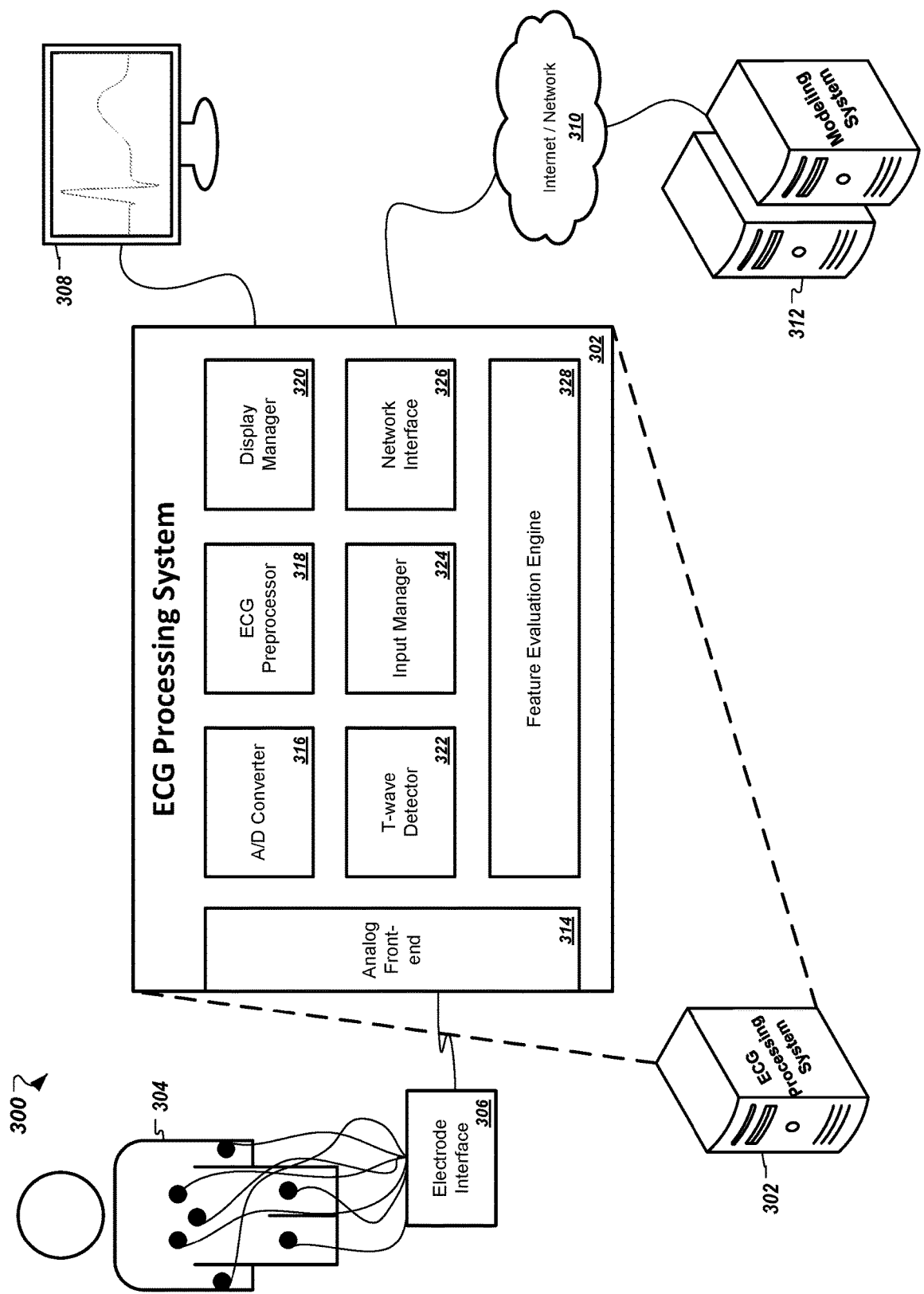
FIG. 3 depicts a block diagram of an example environment of a system for processing, analyzing, and visualizing ECG data.

Referring to FIG. 2, a flowchart is shown of an example process 200 for processing and visualizing ECG data. The process 200 can be carried out by a system of one or more computers in one or more locations, such as the system 300 that FIG. 3 depicts or the computing devices 700, 740 represented in FIG. 7. In some implementations, a computer-based ECG analytical tool may be configured to perform all or some of the stages of the process 200.

At stage 202, the system obtains a set of ECG data, which is generally a recording of the electrical activity of a mammal's heart (e.g. of a patient or other human). The system may load pre-recorded and pre-stored ECG data for an electrocardiogram that had been performed at a past time, or the system may access a real-time stream of ECG data for an electrocardiogram procedure currently being performed. The ECG data may include one or more data channel from each of one or more ECG leads connected to a patient. For example, in a 12-lead surface ECG, the system may collect, store, and process ECG data in separate channels for each of the leads, or for only a subset of the leads as specified by a user. The ECG data that the system collects may be digitized for processing by a digital computing system.

At stage 204, the system pre-processes the ECG data to prepare the data for analysis and presentation. The pre-processing stage can include normalizing levels of the ECG data, filtering the data to remove noise (e.g., high-frequency noise, white noise, power line interference), and at least partially correcting baseline wander that may be present in the original ECG signal. In some implementations, the system may be pre-configured to perform certain pre-processing operations according to default parameters or according to user-specified parameters that have overridden default parameters in whole or in part. In some implementations, the pre-processing can include selecting a subset of one or more channels, from among a plurality of available channels represented in the ECG data, from which to generate processed data that the system can analyze in subsequent stages (e.g., for determination of feature values). For example, the system may determine a score (e.g., signal-to-noise ratio (SNR)) that characterizes the level of noise that occurs in the ECG data from each channel (lead), and may automatically discard those channels that are most noisy. In some implementations, the system may present data characterizing the noise level and other characteristics of the ECG data from each channel to a user, and the user may provide input to the system to cause the system to discard one or more channels indicated by the input.

In some implementations, the system may combine data from multiple leads (channels), from multiple beats, or from both multiple channels and multiple beats to generate one or more representative beats. The system can then analyze the representative beats for the purpose of analysis including, e.g., identifying a T-wave or other segment of a beat, and computing values of one or more T-wave features. A representative beat can be determined in some implementations by averaging data from multiple beats, multiple leads, or both. In some implementations, the system may periodically generate updated representative beats every n seconds (e.g., every 1, 2, 3, 4, 5, or 10 seconds) based on data from a preceding time interval. In some implementations, the representative beat may be constantly updated using a rolling window that, for example, averages the most recent n beats of a patient. In some implementations, the system may automatically discard portions of ECG data corresponding to outlier beats that are deemed to exhibit one or more characteristics that deviate too greatly from a statistical norm.

At stage 206, the system can automatically identify a T-wave represented in the processed ECG data. For example, the system may load a representative beat based on processed ECG data and may compare the representative beat to a template beat to identify different segments of the beat, such as a P-wave, QRS-complex, and T-wave. The template beat may represent a model of different segments of a beat. Based on a result of the comparison, the system may identify the T-wave, for example, by delimiting the portion of the representative beat corresponding to the T-wave with a T-wave start time and a T-wave end time to mark a boundary of the T-wave within the beat.

At stage 208, upon identifying the T-wave represented in the processed ECG data, the system can determine one or more T-wave features values. The T-wave features values may include values for one or more of T-wave left slope, T-wave right slope, T-wave area, T-wave (peak) amplitude, time interval from T-peak to T-end, center of gravity of T-wave in at least one of the x- or y-axis, center of gravity of first quarter of T-wave in at least one of the x- or y-axis, and center of gravity of final quarter of T-wave in at least one of the x- or y-axis.

At stage 210, the system outputs a display of the processed T-wave for one or more beats (or a portion of one beat). The processed T-wave can be displayed on an electronic display screen coupled to the system, such as a desktop LCD monitor or a touchscreen of a mobile computing device. The processed T-wave may be displayed within a graphical user interface that shows a plot or tracing of the T-wave and none, one, or more other portions of the processed ECG for a one or more beats. The user interface may also present graphical elements corresponding to one or more features. All or some of the presented graphical elements may be user-selectable such that the user can manipulate the elements and adjust the corresponding feature values for the elements based on the positions of the elements relative to the plotted ECG signal.

For instance, at stage 212, the system can receive user input that drags one of the feature elements from a first position of the user interface to a second position of the user interface, and in response at stage 214, the system can automatically update the set of feature values for the T-wave. In some implementations, the user can manually manipulate the plotted ECG data by selecting a location on the plotted ECG and dragging the selection by a distance to change the shape of the plotted ECG in a portion of the ECG near the selected location. For example, the user may shift the peak of the T-wave left or right, and may adjust the peak amplitude of the T-wave. Based on the user's manipulation of the plotted ECG, the system may automatically update the set of feature values for the T-wave. In some implementations, the user may enter an adjustment to a feature value, and the system can automatically re-shape the processed ECG wave to accommodate the adjusted feature value. For example, after manually adjusting the ECG features properly, a feature such like T-peak to T-end interval may have been increased by 25 percent, the system can regenerate the processed ECG so that the T-wave has a 25-percent increased T-peak to T-end interval. The system may also re-render the plotted ECG within the graphical user interface to reflect the changes to processed ECG resulting from the adjusted feature value.

Turning to FIG. 3, a block diagram is shown of an example environment 300 of a system for processing, analyzing, and visualizing ECG data. The environment 300 includes a computer-based ECG processing system 302. The system 302 may be implemented as one or more computers in one or more locations, and may include hardware as described with respect to the computing devices 700, 750 in FIG. 7. In some implementations the ECG processing system 302 may be configured to carry out the process 200 of FIG. 2. The processing system 302 can include an analog front-end 314, an analog-to-digital (A/D) converter 316, an ECG pre-processor 318, a display manager 320, a T-wave detector 322, an input manager 324, a network interface 326, and feature evaluation engine 328.

The analog front-end 314 provides connections between the processing system 302 and one or more ECG leads, which in use are affixed to various locations on a patient 304. In some implementations, one or more leads may be connected to input ports of the analog front-end 314. The front-end 314 may provide analog pre-processing of electrical signals sensed by the respective electrode at each of the leads, such as filtering for noise reduction and amplification. In some implementations, the all or some aspects of the analog front-end 314 may be external of the processing system 302. For example, the leads from multiple electrodes may be connected to an external interface 306, which may multiplex the signals into a signal that is communicated to the processing system 302. The A/D converter 316 receives the analog ECG signal, and samples and digitizes the signals from each lead. The ECG pre-processor 318 performs further pre-processing of ECG data output by the A/D converter 316. The pre-processor 318 may implement digital filters and correct baseline wander, for example.

In some implementations, one or more display devices 308 may be communicably coupled to the processing system 320. The display manager 320 can generate a user interface that is presented on the display device 308, which may show a plotted ECG signal and graphical elements corresponding to one or more features of the ECG signal.

The processing system 302 is configured to analyze an ECG signal, identify and label segments of the signal (e.g., P-waves, T-waves), and determine values of features of the signals. The T-wave detector 322 for example may analyze characteristics of an ECG signal to identify and label a T-wave for one or more beats of the ECG signal or for a derived beat representative of beats combined over time and/or multiple leads. The feature evaluation engine 328 determines features values of an ECG signal or a segment of an ECG signal. For example, the feature evaluation engine 328 may determine values for one or more of T-wave left slope, T-wave right slope, T-wave area, T-wave amplitude, T-wave peak to T-wave end interval, or centers of gravity of the entire T-wave or a portion of the T-wave.

In some implementations, the ECG processing system 302 may communicate with a modeling system 312 via a network interface 326 over a communications network 310. Additionally or alternatively, the processing system 302 may include a dedicated modeling system 312 locally as part of the processing system 302. Generally, the modeling system 312 is configured to train and evaluate models to estimate diseases and other patient conditions based at least in part on ECG data or feature values derived from ECG data. The modeling system 312 may obtain data from one or more ECG processing systems that correlates, for each of a plurality of patients, a condition (e.g., disease) known to be associated with the respective patient and feature values derived from an ECG performed on the respective patient. The modeling system 312 may apply statistical analysis to the obtained data to determine a model that indicates values of ECG features or combinations of ECG features that indicate the occurrence of a particular condition. The model can subsequently be evaluated on other patients to determine, based on the values of one or more ECG features of the patient, a likelihood that the patient exhibits one or more specified conditions. For example, as discussed in the following example, a computer-based analytical tool facilitated determination of ECG features as reliable predictors of congenital long-QT syndrome (cLQTS) versus acquired long-QT syndrome (aLQTS)—a distinction with significant diagnostic and management implications.

Figure 5:
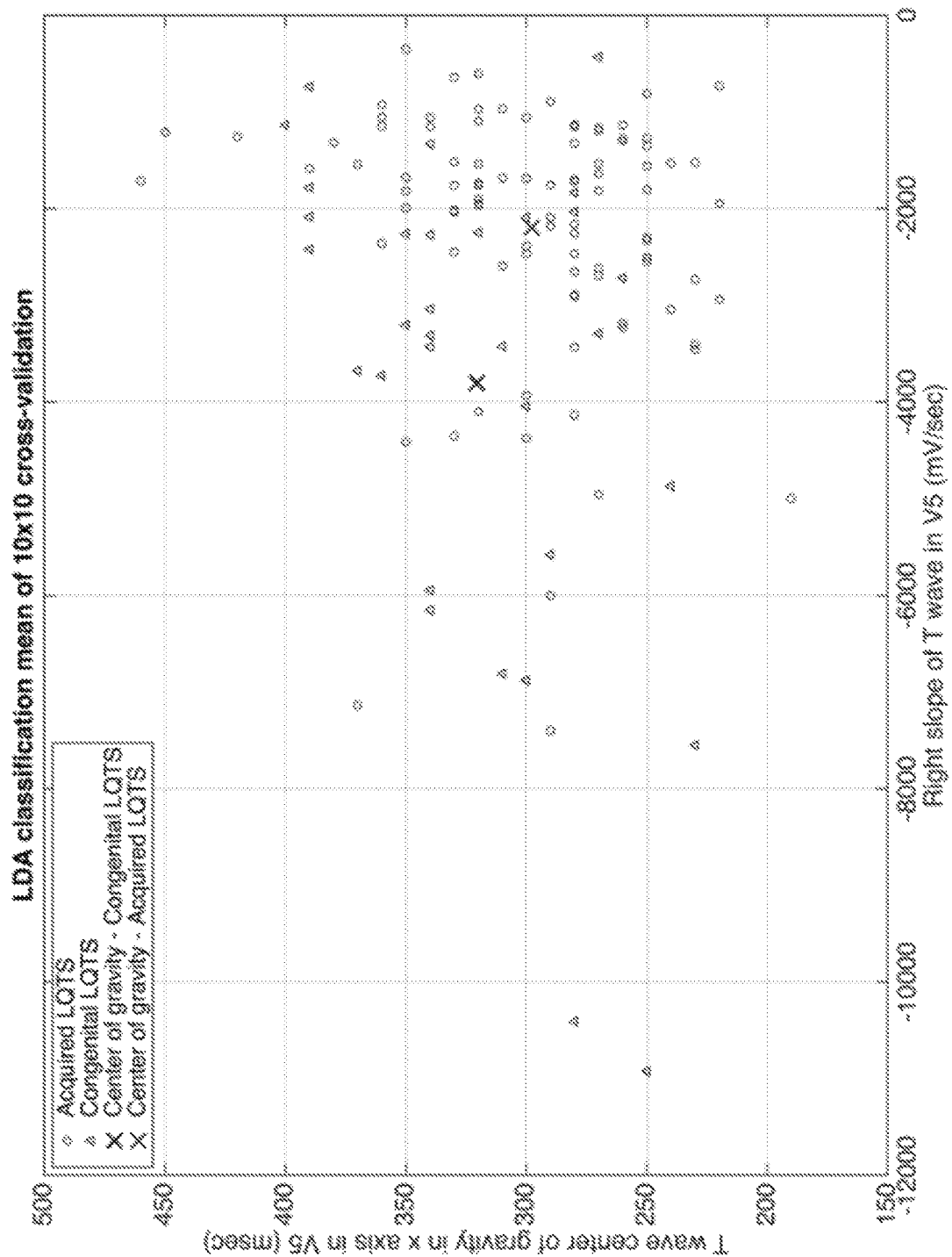
FIG. 5 depicts a scatterplot of LDA classification mean of 10×10 cross-validation, showing T-wave center of gravity in x-axis in V5 vs. right slope of T-wave in V5 in an example study.

FIG. 5 shows results from an example study in which a 12-lead ECG was administered on a cohort of patients. For each lead, the top three selected T-wave features were identified for classifying patients with a given cardiac condition. In some implementations, the systems, methods, devices, and other techniques disclosed herein may derive these T-wave features from patients' ECG data and may use different combinations of features for different leads (e.g., according to the results shown in FIG. 5) to classify a patient as either having or not having a particular cardiac condition, or as being at risk of or not at risk of having the particular cardiac condition. In some implementations, an alert or other indicator may be issued by the system if a patient is determined to have or be at risk of having one or more cardiac conditions.

Example Implementation 1

Study Population. From a collection of more than 52,000 unique electrocardiograms (ECGs) performed at a site over the course of eight months, patients with a prolonged QT were identified though a site-wide QT alert system (n=1145) which screens all ECGs performed at the site and alerts the physician if the QTc is 500 ms or greater. This integrated system works in identification of these patients. See Haugaa K H, Bos J M, Tarrell R F, Morlan B W, Caraballo P J, Ackerman M J. *Institution-wide QT alert system identifies patients with a high risk of mortality*, Mayo Clin Proc 2013; 88:315-25. Briefly, a 12-lead ECG was analyzed by the 12SL ECG analysis program from GE MARQUETTE MEDICAL SYSTEMS or CARDIOLOGY ORG@NIZER from ESAOTE. The following values were extracted from ECGs and ECG reports: patient's age, heart rate, QRS duration, and QTc interval (Bazett formula) and an indicator for the presence of atrial fibrillation or atrial flutter. These measurements were analyzed by an algorithm to determine whether an ECG showed marked QT prolongation, and if this was the case the physician was alerted. Further, every ECG which alerts QT prolongation was manually reviewed to determine the presence of bundle branch block, ventricular pacing, atrial fibrillation, atrial flutter or other supraventricular tachycardias, ST-T changes of typical ischemic origin, and left ventricular hypertrophy which could impact upon the QT interval. If there was presence of any of the above these were excluded. If none of these ECG diagnoses above were present, the ECG was subsequently defined as isolated QTc >500 ms (n=470). Next, those were excluded that did not have QT prolongation secondary to either electrolyte abnormalities (hypokalemia, hypomagnesium, hypocalcaemia) and/or QT prolonging medications (n=417).

Clinical Data. After identification of the patients with isolated QT prolongation, the electronic medical record was reviewed and baseline clinical data, laboratory data (in particular, potassium, magnesium and calcium) and medication were extracted. Hypokalemia was defined as <3.6 mm/L, hypomagnesium <1.7 mg/dL, and hypocalcaemia <4.65 mg/dL (only ionized calcium was used). The values closest to the time of the recorded ECG were used. All medications within 7 days before the alerted ECG were reviewed. QT prolonging medications were defined by its inclusion on the ARIZONA CREDIBLEMEDS QT drug list.

T wave analysis. The flagged 12-lead surface ECG was analyzed using a T-wave analytical tool as described herein. See also Sugrue A, Kremen V, Qiang B, et al., *Electrocardiographic Predictors of Torsadogenic Risk During*

*Dofetilide or Sotalol Initiation: Utility of a Novel T Wave Analysis Program*, Cardiovasc Drugs Ther 2015; Sara J D, Sugrue A, et al., *Electrocardiographic Predictors of Coronary Microvasicular Dysfunction in Patients with Non-Obstructive Coronary Artery Disease: Utility of a Novel T-Wave Analysis Program*, Int J Cardiol. 2016 Jan. 15, available at http://www.ncbi.nlm.nih.gov/pubmed/26580336; Sugrue A., Noseworthy P., et al., *Identification of Concealed and Manifest Long-QT Syndrome Using a Novel T-wave Analysis Program*, Circulation: Arrhythmia and Electrophysiology 2016, available at http://circep.ahaiournals.orq/content/9/7/e003830.short. The features collected for analysis are illustrated, for example, in FIG. 1.

ECG Feature Selection/Statistical approach. To perform ECG feature selection, in each ECG lead a univariate two-sample t-test was performed to pre-select features that showed statistically significantly different means by case status. Features whose mean significantly (p<0.05) differed between cases and controls underwent further analysis. In order to select independent features, Pearson's correlation coefficient was used to examine correlation between pre-selected features. A filter approach was used to find the features with lowest p-value with case status while having low mutual correlation between features. A mutual correlation threshold of features was chosen to be |ρ<0.6|. To evaluate and compare performance of features selected by the filter approach, a 10×10 fold cross-validation using the linear-discriminant analysis (LDA) classifier was used. Given that the final cohort was likely to contain more aLQTS (acquired LQTS) than cLQTS (congenital LQTS), the system randomly matched with a ratio of 1:3 (congenital:acquired). A single lead approach was adopted, for potential ease of use by the physician without relying on multiple leads for determination. Using the ECG features from lead V5, the diagnostic accuracy, sensitivity, specificity, negative predictive value (NPV), and positive predictive values (PPV) were determined for these features to accurately identify the presence of acquired LQTS. A sensitivity analysis was performed to test the robustness of the findings given that demographics (e.g., age) between the acquired and congenital group could be potential confounders. To do this, analysis of aLQTs and cLQTs patients <30 years of age was performed, using the variables that primary analysis would conclude were the best predictors.

Missing data. Leads were excluded from analysis if the T-wave was of low amplitude (<0.1 mV), if interpretation of the T-wave was frustrated from a poor tracing from interference, or if the T-wave was biphasic. If the ECG signal from a lead was not interpretable, the signal recorded from that lead was excluded from the analysis.

Results. In a cohort of 417 patients, with electrocardiographic isolated QT prolongation from either electrolytes and/or QT prolonging medications, 311 ECGs (74%) were analyzed. Within these 311 ECGs, there were 38 patients with cLQTS and 286 with aLQTS. Using the 38 cLQTS, aLQTS cases were randomly selected in a 1:3 ratio, leaving 38 cLQTS and 114 aLQTS as the analysis cohort. The table in FIG. 6 describes the baseline characteristics of this cohort.

In this example, Lead V5 was provided the best discrimination ability, and was subsequently used for analysis. However, this lead was not readable in 6 cLQTS leaving a final cohort of 32 cLQTS and 96 aLQTS. In lead V5, it was observed that patients with aLQTS had a shallower T-wave right slope (−2,322±2,400 vs −3,593±1212 mV/sec, p<0.001), greater Tpeak-Tend interval (109±29 vs 92±31 msec, p<0.001) and smaller T-wave center of gravity of x axis (0.29±4 sec vs 0.31±4 sec, p<0.001).

Prediction. With these three T-wave features, successful identification of congenital vs acquired LQTS was made in 77% of cases with a sensitivity of 90%, specificity of 58%, positive predictive value 83% and negative predictive value 71%. This is represented, for example, in FIG. 5.

Sensitivity Analysis. In a sensitivity analysis, patients under the age of 30 years (n=50 patients, 29 cLQTs, 21 aLQTS) were exclusively evaluated. Within this population, the results remained robust. Using the determined features above (T-wave right slope, Tpeak-Tend Interval, and T-wave center of gravity x-axis), the underlying etiology of the prolonged QT (aLQTS vs cLQTS) was predicted in 78.3% of cases.

Discussion. When a clinician is faced with a patient who has QT prolongation, particularly in those cases with an abnormal QTc (e.g., QTc >500 ms), the underlying etiology can be unclear at the time the QT prolongation is noted. Utilizing automated T-wave analysis, subtle variations in cardiac repolarization were detected from which the underlying etiology (aLQTS vs cLQTS) was identified. The ability to distinguish aLQTS from cLQTS can have significant clinical importance, and can inform subsequent management strategies and prognosis. The features of the T-wave analysis tool discussed herein can enable detection of the subtle ECG features that are used to determine a particular patient condition (e.g., the underlying etiology for patients with abnormal QTc).

The mechanism behind acquired long QT prolongation can be largely due to changes in the $I_{kr}$ channel (which can be a critical channel in the phase 3 repolarisation of the cardiac action potential), which manifest in T wave repolarisation changes. Drugs that are known to cause prolongation of the QT are often related to the blockage of the $I_{kr}$ channel, though there is some evidence that $I_{ks}$ and $I_{NA}$ may also be involved. See Veerman C C, Verkerk A O, Blom M T, et al., Slow delayed rectifier potassium current blockade contributes importantly to drug-induced long QT syndrome, *Circ Arrhythm Electrophysiol* 2013; 6:1002-9. Hypokalemia predisposes to prolongation through subsequent modification of the function of the $I_{kr}$ channel. Specifically, this modification may be a decrease in $I_{kr}$ by enhanced inactivation (see Yang T, Snyders D J, Roden D M. *Rapid inactivation determines the rectification and [K+]o dependence of the rapid component of the delayed rectifier K+ current in cardiac cells*, Circ Res 1997; 80:782-9) or exaggerated competitive block by sodium (see Numaguchi H, Johnson J P, Jr., Petersen C I, Balser J R, *A sensitive mechanism for cation modulation of potassium current*, Nat Neurosci 2000; 3:429-30). Interesting extracellular potassium is a critical determinant of drug block of $I_{kr}$ (see Yang T, Roden D M. Extracellular potassium modulation of drug block of IKr, Implications for torsade de pointes and reverse use-dependence, Circulation 1996; 93:407-11), which can have significant implications for clinical practice, and why potassium replacement in those receiving drugs that cause $I_{kr}$ blockade can be important. Hypomagnesium is related due to its ability to directly cause hypokalemia. However it too has its own potential mechanisms, with influence of the inward rectification of the potassium channels (see Matsuda H., *Magnesium gating of the inwardly rectifying K+ channel*, Annu Rev Physiol 1991; 53:289-98; Vandenberg C A, *Inward rectification of a potassium channel in cardiac ventricular cells depends on internal magnesium ions*, Proc Natl Acad Sci USA 1987; 84:2560-4), as well as its potential impact upon the L type calcium channels (see Kannankeril P, Roden D M, Darbar D, *Drug-induced long QT syndrome*, Pharmacol Rev 2010; 62:760-81). In the example discussed here, different changes in these channels were detected, in particular $I_{kr}$, which manifest as T wave repolarisation abnormalities. For example, T-wave right slope and Tpeak-Tend can be markers of $I_{kr}$ channel dysfunction.

In some applications, T-wave analysis using the tool described herein can be performed for drug screening for potential $I_{kr}$ activity. QT prolongation is an imperfect surrogate for torsadogenic potential (see Hondeghem L M, *Thorough QT/QTc not so thorough: removes torsadogenic predictors from the T-wave, incriminates safe drugs, and misses profibrillatory drugs*, Journal of cardiovascular electrophysiology 2006; 17:337-40; Antzelevitch C, Shimizu W, *Cellular mechanisms underlying the long QT syndrome*, Current opinion in cardiology 2002; 17:43-51; Yap Y G, Camm A J, *Drug induced QT prolongation and torsades de pointes*, Heart 2003; 89:1363-72; Thomsen M B, Volders P G, Beekman J D, Matz J, Vos M A, *Beat-to-Beat variability of repolarization determines proarrhythmic outcome in dogs susceptible to drug-induced torsades de pointes*, Journal of the American College of Cardiology 2006; 48:1268-76) since the risk of TdP is neither a linear function of the baseline QT interval nor of the extent of QT interval prolongation during drug administration (see Roden D M, *Drug-induced prolongation of the QT interval*, The New England journal of medicine 2004; 350:1013-22), and a better/complementary marker of risk, such as T-wave right slope and TpTe interval can be used. T-wave right slope as identified in this example was is also correlated with TdP in patients loaded with sotaolol and dofetilide. See Sugrue A, Kremen V, Qiang B, et al, *Electrocardiographic Predictors of Torsadogenic Risk During Dofetilide or Sotalol Initiation: Utility of a Novel T Wave Analysis Program*, Cardiovasc Drugs Ther 2015; 29:433-41. In addition the TpTe interval is considered a good marker for arrhythmogenic risk. See Letsas K P, Weber R, Astheimer K, Kalusche D, Arentz T, *Tpeak-Tend interval and Tpeak-Tend/QT ratio as markers of ventricular tachycardia inducibility in subjects with Brugada ECG phenotype*, Europace 2010; 12:271-4; Gupta P, Patel C, Patel H, et al., *T(p-e)/QT ratio as an index of arrhythmogenesis*, Journal of electrocardiology 2008; 41:567-74. Prolongation of this interval can increase the period when potential fatal re-entry ventricular tachycardias can occur and has been linked to arrhythmogenesis in long QT syndromes (see Topilski I, Rogowski O, Rosso R, et al., *The morphology of the QT interval predicts torsade de pointes during acquired bradyarrhythmias*, Journal of the American College of Cardiology 2007; 49:320-8), hypertrophic cardiomyopathy (see Shimizu M, Ino H, Okeie K, et al., *T-peak to T-end interval may be a better predictor of high-risk patients with hypertrophic cardiomyopathy associated with a cardiac troponin I mutation than QT dispersion*, Clinical cardiology 2002; 25:335-9), patients receiving primary percutaneous coronary intervention for an MI (see Haarmark C, Hansen P R, Vedel-Larsen E, et al., *The prognostic value of the Tpeak-Tend interval in patients undergoing primary percutaneous coronary intervention for ST-segment elevation myocardial infarction*, Journal of electrocardiology 2009; 42:555-60), and Brugada syndrome (see Letsas K P, Weber R, Astheimer K, Kalusche D, Arentz T, *Tpeak-Tend interval and Tpeak-Tend/QT ratio as markers of ventricular tachycardia inducibility in subjects with Brugada ECG phenotype*. Europace 2010; 12:271-4).

Limitations: aLQTS and cLQTS patients were not matched for demographic characteristics that could also be potentially associated with repolarization, however the sensitivity analysis indicate robust results. Some patients with aLQTS may harbor functional common polymorphisms that predispose them to QT prolongation and risk of sudden death. See Yang P, Kanki H, Drolet B, et al., *Allelic variants in long-QT disease genes in patients with drug-associated torsades de pointes*, Circulation 2002; 105:1943-8; Lehtonen A, Fodstad H, Laitinen-Forsblom P, Toivonen L, Kontula K, Swan H., *Further evidence of inherited long QT syndrome gene mutations in antiarrhythmic drug-associated torsades de pointes*, Heart Rhythm 2007; 4:603-7. The genetic background in the population of people with aLQTS in this example was generally unknown. However, if the population of patients did harbor these mutations, the T wave analysis was still able to differentiate between those with manifest cLQTS and those with these potential polymorphism.

Example Implementation 2

Summary: In this example study, 407 genetically confirmed LQT1 (n=246, 43% male) and LQT2 (n=161, 41% male) patients were analyzed over the mean follow-up period of 6.4±3.9 years. ECG analysis was conducted using T-wave analysis techniques like those described herein, which quantitates subtle changes in T wave morphology. Time to a LQTS-associated cardiac event was analyzed using Cox proportional hazards regression methods. The study identified 23 patients who experienced ≥1 defined breakthrough cardiac arrhythmic events with 5- and 10-year event rates of 4% and 7%. Two independent predictors of future LQTS-associated cardiac events from the surface ECG were identified: left slope of T wave in lead V6 (HR=0.40 [0.24-0.69], p<0.001) and T wave center of gravity x axis (last 25% of wave) in Lead I (HR=1.90 [1.21-2.99], p=0.005), c-statistic of 0.77 (0.65-0.89). When added to the QTc (c-statistic 0.68 for QTc alone), discrimination improved to 0.78. Genotype analysis showed weaker association between these T wave variables and LQT1-triggered events while these features were stronger in patients with LQT2 and significantly outperformed the QTc [C statistic—0.82 (0.71-0.93)].

Methods: Institutional review board approval was obtained for this study. 661 patients with LQTS, who were evaluated and treated at MAYO CLINIC between 1999 and 2015, formed the initial cohort. In this cohort, genetic testing was positive in 596 patients (90%), of whom 287 (43%) were LQT1 (KCNQ1), 204 (31%) were LQT2 (KCNH2), 56 (9%) were LQT3 (SCNSA), 20 (3%) were LQT4-17 (minor genes), and 29 (4%) had multiple LQTS-associated mutations. Subsequently, excluded LQT3-17 patients were excluded because of their smaller sample sizes. The final cohort therefore contained only patients with either LQT1 or LQT2 (n=491). Patients were excluded who had an unreadable ECG either due to either unreadable T waves [Biphasic T-wave (e.g., a T wave that crosses the isoelectric line a positive and a negative deflection), small amplitude <0.1 mV], ventricular paced rhythm, presence of a bundle branch block, or atrial fibrillation (n=84). The primary outcome evaluated was the occurrence of an LQTS-related breakthrough cardiac event (BCE), which was defined as arrhythmogenic syncope, seizure, aborted cardiac arrest (ACA), appropriate implantable cardioverter defibrillator (ICD) shock, or sudden cardiac death (SCD) after their first evaluation at a specialty center. Events were abstracted from the electronic medical record by two authors (A.S and R.R) with M.J.A. providing final adjudication when there was disagreement.

The study analyzed the first ECG recorded with the initial consultation. The 12-lead surface ECG was analyzed using the T-wave analysis techniques described herein. See Sugrue A, Kremen V, Qiang B, et al. Electrocardiographic predictors of torsadogenic risk during dofetilide or sotalol initiation: utility of a novel T wave analysis program. *Cardiovascular drugs and therapy* 2015; 29(5):433-41. The raw, 12-lead ECG tracings were uploaded into the automated T-wave analysis software tool. Pre-processing procedures were applied to enable de-noising and baseline correction. This was followed by ECG feature extraction using the T-wave analysis tool, which implements the analysis techniques discussed herein. ECG features (mentioned below) from the ECG are detected by a Bayesian statistical peak delineation algorithm.[12] The analysis tool was configured to analyze multiple beats over a ten second ECG strip. The operator of the analysis tool was unaware of the arrhythmic event status of the subject when analyzing the 12-lead surface ECG. The QTc was calculated (Bazett's formula; QTc=QT√[HR/60]) using the clinical 12-lead ECG (MARQUETTE™ 12SL™ ECG Analysis Program, GENERAL ELECTRIC HEALTHCARE), Leads were excluded from analysis if the T wave was of low amplitude (<0.1 mV) or if there was Biphasic T-wave inversion, due to the limits this creates on ECG and in particular T wave analysis. If a lead or a variable was missing >20% of values, this was excluded from the final analysis. For the remaining leads (I, II, V4, V5, V6, aVR), missing values were imputed.

Baseline variables are presented as number and percentage or with median and quartiles, as appropriate. Due to the nature of the distribution of some ECG parameters and to minimize potential effects of outliers, all ECG parameters were categorized into quartiles (1,2,3,4), and then analyzed as an ordinal trend across these quartiles. Time to event analyses were used to examine the occurrence of first LQTS-related BCE after this analyzed ECG and subjects without any such events were censored at last available clinical follow-up. Incidence of LQTS-associated BCEs was estimated using Kaplan-Meier methods. As mentioned above Leads I, II, V4, V5, V6 and aVR were used for this analysis. Due to the number of ECG parameters in relation to the number of subjects and events, we chose to use a leave one out cross validation for model selection to minimized overfitting. Essentially, this method uses a score selection method within Cox proportional hazards regression and counts the number of times each parameter is entered into the model across all 407 leave one out cross validation sets. The final model is chosen based on the number of times each variable is chosen. See Rushing C, Bulusu A, Hurwitz H I, et al. A leave-one-out cross-validation SAS macro for the identification of markers associated with survival. *Comput Biol Med* 2015; 57:123-9. doi: 10.1016/j.compbiomed.2014.11.015. After the final set of ECG parameters was chosen, the model was fit on the entire set of data and results were summarized with hazard ratio and associated 95% confidence limits. Association of QTc and beta blocker use with LQTS-associated BCEs was then evaluated in models with chosen ECG parameters. As a measure of ability of the model to discriminate those with and without BCEs, survival c-statistics were also estimated and validated using a leave one out cross validation approach. Subgroup analyses were also conducted within each genotype group, but due to sample size, the model selection was not repeated within these subgroups. Analyses were done using SAS version 9.4 and two-sided p-values <0.05 were considered to be statistically significant.

Results: The final study cohort was comprised of 246 patients (43% male) with LQT1 and 161 patients (41% male) with LQT2. Clinical characteristics of the total population are shown in Table 1:

TABLE 1

Baseline Demographics

| Variable | Overall (N = 407) |
|---|---|
| Age at First Mayo Clinic ECG, median in years (Q1, Q3) | 16 (10, 34) |
| Gender, n (%) | |
| Female | 235 (58%) |
| Male | 172 (42%) |
| BB, n (%) | 181 (44%) |
| LCSD, n (%) | 50 (12%) |
| ICD, n (%) | 77 (19%) |
| FH LQTS, n (%) | 313 (77%) |
| FH SCA, n (%) | 190 (47%) |
| LQTS Genetic subtype, n (%) | |
| LQT1 | 246 (60%) |
| LQT2 | 161 (40%) |
| T4_COG_X_LEAD_I, median (Q1, Q3) | 0.36 (0.34, 0.40) |
| T_LSLOPE_LEAD_V6, median (Q1, Q3) | 2093.4 (1208.8, 3127.0) |
| QTc, median in ms (Q1, Q3) | 455.00 (433.00, 483.00) |
| KM Event, K-M (# events) | |
| 1 Years | 0.98 (8) |
| 2 Years | 0.97 (10) |
| 3 Years | 0.96 (14) |
| 4 Years | 0.96 (16) |
| 5 Years | 0.95 (16) |
| 10 Years | 0.93 (21) |
| 15 Years | 0.88 (23) |

BB—Beta blocker,
FH—Family history,
ICD—implantable cardioverter defibrillator,
LCSD—left cardiac sympathetic denervation,
SCA—Sudden cardiac arrest,
T4_COG_X—T wave centre of gravity on the x axis (last 25% of the T wave),
T_LSLOPE—T wave Left slope Table 2 describes the baseline characteristics per LQTS genotype:

TABLE 2

Genotype Distributions

| Variable | LQT1 (N = 246) | LQT2 (N = 161) | P Value |
|---|---|---|---|
| Age at First Mayo Clinic ECG, median in years (Q1, Q3) | 16 (9, 34) | 17 (11. 33) | 0.83 |
| Gender, n (%) | | | 0.74 |
| Female | 140 (57%) | 95 (59%) | |
| Male | 106 (43%) | 66 (41%) | |
| BB, n (%) | 101 (41%) | 80 (50%) | 0.11 |
| LCSD, n (%) | 33 (13%) | 17 (11%) | 0.26 |

TABLE 2-continued

Genotype Distributions

| Variable | LQT1 (N = 246) | LQT2 (N = 161) | P Value |
|---|---|---|---|
| ICD, n (%) | 26 (11%) | 51 (32%) | <.001 |
| FH LQTS, n (%) | 193 (78%) | 120 (75%) | 0.46 |
| FH SCA, n (%) | 126 (51%) | 64 (40%) | 0.03 |
| T4_COG_X_LEAD_I, median (Q1, Q3) | 0.36 (0.34, 0.39) | 0.36 (0.33, 0.39) | 0.31 |
| T_LSLOPE_LEAD_V6, median (Q1, Q3) | 2585.2 (1823.5, 3745.3) | 1373.6 (846.06, 2286.2) | <.001 |
| QTc, median in ms (Q1, Q3) | 456.5 (433.0, 485.0) | 455.0 (435.0, 483.0) | 0.98 |
| KM Event, K-M (# events) | | | 0.03 |
| 1 Years | 0.99 (3) | 0.97 (5) | |
| 2 Years | 0.99 (3) | 0.96 (7) | |
| 3 Years | 0.98 (4) | 0.93 (10) | |
| 4 Years | 0.98 (4) | 0.92 (12) | |
| 5 Years | 0.98 (5) | 0.92 (12) | |
| 10 Years | 0.97 (6) | 0.88 (15) | |
| 15 Years | 0.89 (8) | 0.88 (15) | |

BB—Beta blocker,
FH—Family history,
ICD—implantable cardioverter defibrillator,
LCSD—left cardiac sympathetic denervation,
SCA—Sudden cardiac arrest,
T4_COG_X—T wave centre of gravity on the x axis (last 25% of the T wave),
T_LSLOPE—T wave Left slope Table 3 shows that the mean follow-up period of 6.4±3.9 years, 23 patients experienced ≥1 defined BCEs with 5- and 10-year event rates of 4% and 7%

TABLE 3

LQTS Event Cohort Demographics

| Variable | Overall (N = 23) |
|---|---|
| Age at First Mayo Clinic ECG, median in years (Q1, Q3) | 15 (12, 23) |
| Gender, n (%) | |
| Female | 15 (78%) |
| Male | 5 (22%) |
| BB, n (%) | 16 (70%) |
| LCSD, n (%) | 13 (57%) |
| ICD, n (%) | 19 (83%) |
| FH LQTS, n (%) | 12 (52%) |
| FH SCA, n (%) | 9 (39%) |
| LQTS Genetic subtype, n (%) | |
| LQT1 | 8 (35%) |
| LQT2 | 15 (65%) |
| Number BCEs, median (Q1, Q3) | 1 (1, 3) |

SB—Beta blocker,
BCE—breakthrough cardiac events,
FH—Family history,
ICD—implantable cardioverter defibrillator,
LCSD—left cardiac sympathetic denervation, Analysis of the total LQT1 and LQT2 cohort with multivariable cox proportional hazards regression identified two independent predictors of future LQTS-associated BCEs from the surface ECG; left slope of T wave in lead V6 and T wave center of gravity (COG) x axis (last 25% of wave) in Lead I (Table 4). These results remained consistent after being adjusted for the patient's individual QTc value. Each quartile increase in left slope T wave was associated with a decreased risk of BCEs (HR=0.40 [0.24-0.69], p<0.001), while increasing quartiles of COG x axis (ie. a COG further along the x axis, HR=1.90 [1.21-2.99], p=0.005) and quartile increase in QTc (HR=1.65 [1.05-2.59], p=0.03) were associated with increased risk of BCEs. FIG. 2 shows the Kaplan Meier event free survival for the selected T wave features and QTc stratified by quartiles [1A-T wave COG x axis (last 25% of wave), 1B-T wave left slope, and 1C-QTc].

The discriminative powers of the selected features were also evaluated using cross-validation c-statistics. Importantly, the ECG features show additive value to the QTc. The combination of the left slope of T wave in Lead V6 and T wave COG x axis (last 25% of wave) in Lead I resulted in a c-statistic of 0.77 (0.65-0.89). This was better than the QTc alone 0.68 (0.58-0.77). In a model with all three features, the c-statistic slightly improved to 0.78 (0.67-0.90).

Genotype-Specific Analysis: When examined specifically by genotype (Table 5), in LQT1, there was an inverse association with the left slope of the T wave in V6 and risk of BCEs (HR=0.44 [0.21-0.91], p=0.03 per quartile), but no association with quartiles of COG x axis (HR=1.32 [0.71-2.46], p=0.38). Although increasing quartiles of QTc was non-significant when adjusting for the other T wave variables (HR=1.69 [0.8-3.6], p=0.17), it was marginally associated with increased risk of events in univariate analysis (HR=2.1 [1.1-4.4], p=0.06). The cross-validated C statistic with all three features in LQT1 was moderate at 0.59 (0.35-0.83).

TABLE 5

Multivariate Cox Analysis for LQT1. Model 1) Independent ECG features and 2) Addition of QTc to the model

| Model | ECG features | Hazard Ratio | 95% CI | p |
|---|---|---|---|---|
| 1 | Left slope of T wave in Lead V6 | 0.44 | 0.21-0.91 | 0.03 |
| | T wave COG x axis (last 25% of wave) in Lead I | 1.32 | 0.71-2.46 | 0.38 |
| 2 | Left slope of T wave in Lead V6 | 0.48 | 0.23-1.00 | 0.05 |
| | T wave COG x axis (last 25% of wave) in Lead I | 1.22 | 0.64-2 53 | 0.55 |
| | QTc | 1.69 | 0.80-3.56 | 0.17 |

In contrast, for patients with LQT2 (Table 6), each quartile increase in left slope T wave, was associated with a borderline decrease in risk of events (HR=0.41 [0.16-1.0], p=0.06), while increasing quartiles of COG x axis (HR=3.2 [1.6-6.4], p=0.001) was associated with an increased risk of events. Adjusted for T wave features, QTc quartiles (HR=1.54 [0.9-2.8], p=0.14) were not significantly associated with risk of LQT2-associated BCEs. The cross-validated C statistic with all three features was strong at 0.82 (0.71-0.93).

TABLE 6

Multivariate Cox Analysis for LQT2. 1) Independent ECG features and 2) Addition of QTc to the model

| Model | ECG features | Hazard Ratio | 95% CI | p |
|---|---|---|---|---|
| 1 | Left slope of T wave in Lead V6 | 0.41 | 0.16-1.04 | 0.06 |
|   | T wave COG x axis (test. 25% of wave) in Lead I | 3.20 | 1.60-6.41 | 0.001 |
| 2 | Left slope of T wave in Lead V6 | 0.47 | 0.19-1.18 | 0.11 |
|   | T wave COG x axis (test 25% of wave) in Lead I | 2.68 | 1.34-5.37 | 0.006 |
|   | QTc | 1.55 | 0.86-2.77 | 0.14 |

Beta Blocker Therapy: In a secondary analysis controlling for beta blocker therapy (which was recorded at time of ECG analysis), similar risks were observed. There was good discrimination in the overall cohort, with limited discrimination in LQT1 and strong discrimination in LQT2.

Discussion: Comprehensive T wave morphological and morphometric analysis (aka, the "T wave fingerprint") can discriminate patients with concealed LQTS from healthy controls. See also Sugrue A, Noseworthy P A, Kremen V, et al. *Identification of Concealed and Manifest Long QT Syndrome Using a Novel T Wave Analysis Program. Circulation: Arrhythmia and Electrophysiology* 2016; 9(7): e003830. A significant finding of this example study was the identification of a set of surface ECG markers with the power to predict breakthrough arrhythmic events particularly in patients being treated for the second most common LQTS genotype, namely LQT2. Specifically, the T wave left slope in Lead V6 and the T wave COG x axis (last 25% of wave) in Lead I were able to identify those LQT2 patients at higher risk of future events. These findings potentially create an enhanced path towards personalized clinical approaches for patients with LQTS. Some treatment options include: beta blocker therapy, left cardiac sympathetic denervation (LCSD), and an implantable cardioverter defibrillator (ICD).

Clinical Applications: The instant example has highlights ECG markers that predict breakthrough arrhythmic risk in LQTS, particularly in LQT2. Predicting breakthrough arrhythmic risks based on analysis of surface ECGs according to techniques discussed herein may have broad clinical application, since the ECG is inexpensive and universally performed in patients with LQTS. Ultimately, this approach could improve risk stratification and facilitate personalized care that targets intensification of the LQT2-directed treatment program to those at highest risk. A physician and/or patient can make better informed decisions and provide a window into the likelihood of future events among those who are currently "asymptomatic".

Conclusion: Architectural T wave analysis and the generation of a "T wave fingerprint" from the surface ECG can enhance risk stratification for patients with LQTS, especially LQT2. In particular, a decreasing T wave left slope and an increasing T wave COG x-axis (last 25% of the wave) can help identify those who remain at increased risk of a LQT2-triggered BCE. This has the potential to help define an individualized targeted therapeutic approach and further refine clinical decision-making.

Figure 7:
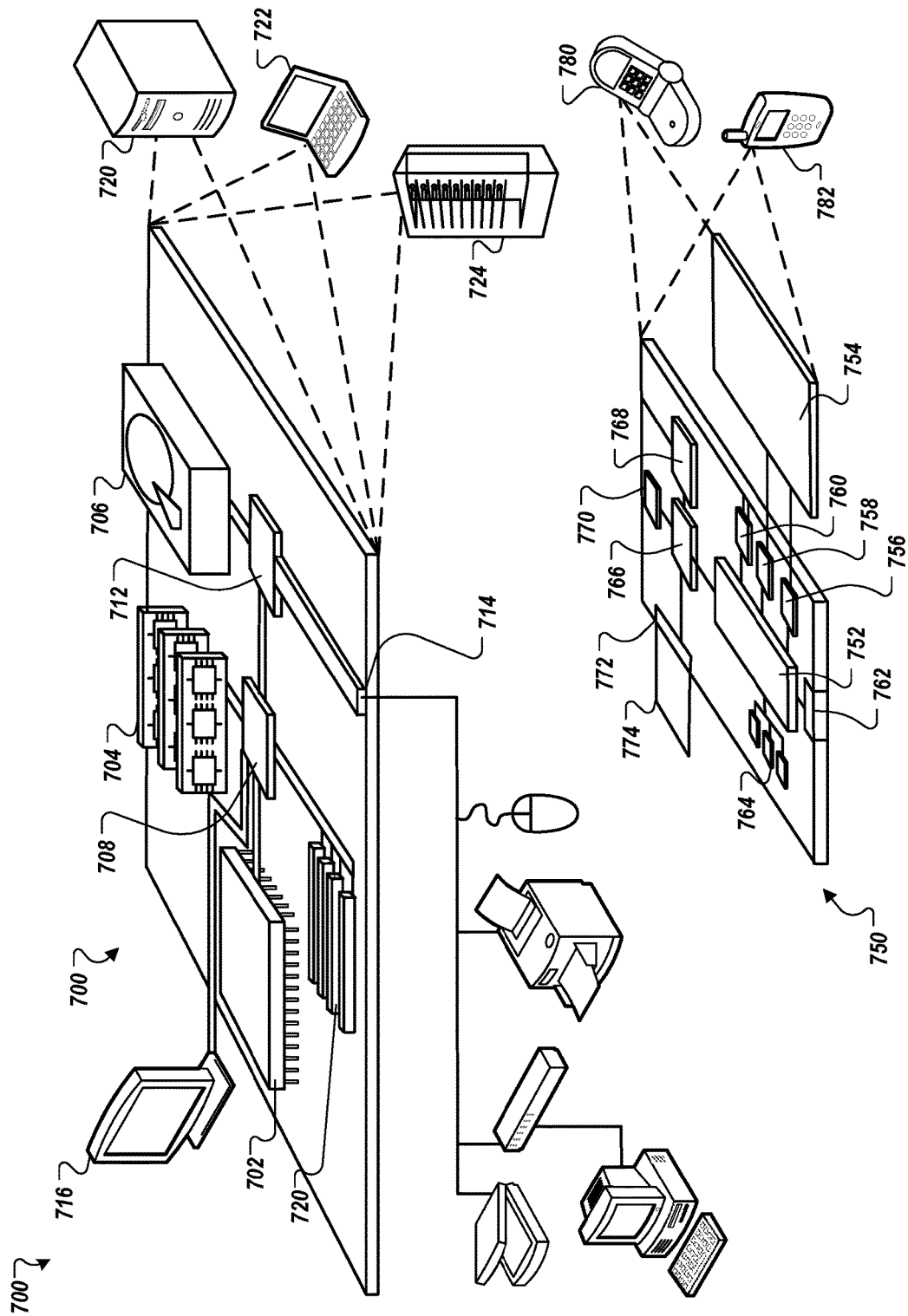
FIG. 7 is a block diagram of computing devices that may be used to implement the systems and methods described in this document, as either a client or as a server or plurality of servers.

FIG. 7 is a block diagram of computing devices 700, 750 that may be used to implement the systems and methods described in this document, as either a client or as a server or plurality of servers. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. Additionally computing device 700 or 750 can include Universal Serial Bus (USB) flash drives. The USB flash drives may store operating systems and other applications. The USB flash drives can include input/output components, such as a wireless transmitter or USB connector that may be inserted into a USB port of another computing device. The components shown here, their connections and relationships, and their functions, are meant to be exemplary only, and are not meant to limit implementations described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and may be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses may be used, as appropriate, along with multiple memories and types of memory. Also, multiple computing devices 700 may be connected, with each device providing portions of the necessary operations (e.g., as a server bank, a group of blade servers, or a multi-processor system).

The memory 704 stores information within the computing device 700. In one implementation, the memory 704 is a volatile memory unit or units. In another implementation, the memory 704 is a non-volatile memory unit or units. The memory 704 may also be another form of computer-readable medium, such as a magnetic or optical disk.

The storage device 706 is capable of providing mass storage for the computing device 700. In one implementation, the storage device 706 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 704, the storage device 706, or memory on processor 702.

The high speed controller 708 manages bandwidth-intensive operations for the computing device 700, while the low speed controller 712 manages lower bandwidth-intensive operations. Such allocation of functions is exemplary only.

In one implementation, the high-speed controller 708 is coupled to memory 704, display 716 (e.g., through a graphics processor or accelerator), and to high-speed expansion ports 710, which may accept various expansion cards (not shown). In the implementation, low-speed controller 712 is coupled to storage device 706 and low-speed expansion port 714. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 700 may be implemented in a number of different forms, as shown in the figure. For example, it may be implemented as a standard server 720, or multiple times in a group of such servers. It may also be implemented as part of a rack server system 724. In addition, it may be implemented in a personal computer such as a laptop computer 722. Alternatively, components from computing device 700 may be combined with other components in a mobile device (not shown), such as device 750. Each of such devices may contain one or more of computing device 700, 750, and an entire system may be made up of multiple computing devices 700, 750 communicating with each other.

Computing device 750 includes a processor 752, memory 764, an input/output device such as a display 754, a communication interface 766, and a transceiver 768, among other components. The device 750 may also be provided with a storage device, such as a microdrive or other device, to provide additional storage. Each of the components 750, 752, 764, 754, 766, and 768, are interconnected using various buses, and several of the components may be mounted on a common motherboard or in other manners as appropriate.

The processor 752 can execute instructions within the computing device 750, including instructions stored in the memory 764. The processor may be implemented as a chipset of chips that include separate and multiple analog and digital processors. Additionally, the processor may be implemented using any of a number of architectures. For example, the processor 752 may be a CISC (Complex Instruction Set Computers) processor, a RISC (Reduced Instruction Set Computer) processor, or a MISC (Minimal Instruction Set Computer) processor. The processor may provide, for example, for coordination of the other components of the device 750, such as control of user interfaces, applications run by device 750, and wireless communication by device 750.

Processor 752 may communicate with a user through control interface 758 and display interface 756 coupled to a display 754. The display 754 may be, for example, a TFT (Thin-Film-Transistor Liquid Crystal Display) display or an OLED (Organic Light Emitting Diode) display, or other appropriate display technology. The display interface 756 may comprise appropriate circuitry for driving the display 754 to present graphical and other information to a user. The control interface 758 may receive commands from a user and convert them for submission to the processor 752. In addition, an external interface 762 may be provide in communication with processor 752, so as to enable near area communication of device 750 with other devices. External interface 762 may provide, for example, for wired communication in some implementations, or for wireless communication in other implementations, and multiple interfaces may also be used.

The memory 764 stores information within the computing device 750. The memory 764 can be implemented as one or more of a computer-readable medium or media, a volatile memory unit or units, or a non-volatile memory unit or units. Expansion memory 774 may also be provided and connected to device 750 through expansion interface 772, which may include, for example, a SIMM (Single In Line Memory Module) card interface. Such expansion memory 774 may provide extra storage space for device 750, or may also store applications or other information for device 750. Specifically, expansion memory 774 may include instructions to carry out or supplement the processes described above, and may include secure information also. Thus, for example, expansion memory 774 may be provide as a security module for device 750, and may be programmed with instructions that permit secure use of device 750. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 774, or memory on processor 752 that may be received, for example, over transceiver 768 or external interface 762.

Device 750 may communicate wirelessly through communication interface 766, which may include digital signal processing circuitry where necessary. Communication interface 766 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 768. In addition, short-range communication may occur, such as using a Bluetooth, WiFi, or other such transceiver (not shown). In addition, GPS (Global Positioning System) receiver module 770 may provide additional navigation- and location-related wireless data to device 750, which may be used as appropriate by applications running on device 750.

Device 750 may also communicate audibly using audio codec 760, which may receive spoken information from a user and convert it to usable digital information. Audio codec 760 may likewise generate audible sound for a user, such as through a speaker, e.g., in a handset of device 750. Such sound may include sound from voice telephone calls, may include recorded sound (e.g., voice messages, music files, etc.) and may also include sound generated by applications operating on device 750.

The computing device 750 may be implemented in a number of different forms, as shown in the figure. For example, it may be implemented as a cellular telephone 780. It may also be implemented as part of a smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

Although a few implementations have been described in detail above, other modifications are possible. Moreover, other mechanisms quantifying potassium based on ECG data may be used. In addition, the logic flows depicted in the figures do not require the particular order shown, or sequential order, to achieve desirable results. Other steps may be provided, or steps may be eliminated, from the described flows, and other components may be added to, or removed from, the described systems. Accordingly, other implementations are within the scope of the following claims.

What is claimed is:

1. A method, comprising:
    receiving, by a computing system, a set of data that characterizes an electrocardiogram of a patient having abnormal QT prolongation;
    analyzing, by the computing system, the set of data that characterizes the electrocardiogram of the patient to identify a T-wave that occurs in the electrocardiogram;
    determining, by the computing system and in response to identifying a T-wave that occurs in the electrocardiogram, values of one or more features of the T-wave, wherein the one or more features of the T-wave comprise at least one of T-wave left slope or T-wave center of gravity;
    determining, based on the values of the one or more features of the T-wave, a prediction of the patient's risk of experiencing a future long QT-syndrome (LQTS) associated cardiac event and
    providing an indication of the prediction of the patient's risk of experiencing the future LQTS-associated cardiac event.

2. The method of claim 1, wherein analyzing the set of data that characterizes the electrocardiogram of the patient to identify the T-wave that occurs in the cardiogram comprises automatically identifying a particular segment of the electrocardiogram that corresponds to the T-wave, from among a plurality of segments of the electrocardiogram that correspond to different portions of the electrocardiogram that include the T-wave and at least one of a P-wave or a QRS-complex.

3. The method of claim 2, further comprising:
    displaying, in a graphical user interface on an electronic display coupled to the computing system, a visual representation of the electrocardiogram for one or more heartbeats of the patient; and
    in conjunction with displaying the visual representation of the electrocardiogram, visually marking the particular segment of the electrocardiogram that corresponds to the T-wave.

4. The method of claim 3, further comprising in conjunction with displaying the visual representation of the electrocardiogram, visually marking a second segment of the electrocardiogram that corresponds to the QRS-complex.

5. The method of claim 3, further comprising:
    while displaying the visual representation of the electrocardiogram, providing a control in the graphical user interface that allows a user to confirm or reject the particular segment of the electrocardiogram that the computing system automatically identified as corresponding to the T-wave of the patient's heartbeat; and
    receiving input that indicates user selection of the control and a confirmation or rejection of the particular segment of the electrocardiogram as corresponding to the true T-wave of the patient's heartbeat.

6. The method of claim 3, further comprising adjusting a boundary of the particular segment of the electrocardiogram that corresponds to the T-wave of the patient's heartbeat according to user input that specifies the adjustment.

7. The method of claim 1, comprising:
    receiving raw data that characterizes the electrocardiogram of the patient; and
    processing the raw data to generate modified data that characterizes the electrocardiogram of the patient, wherein the computing system performs at least one of the analyzing step or the determining step with respect to the modified data.

8. The method of claim 7, wherein processing the raw data that characterizes the electrocardiogram of the patient comprises at least one of removing noise from the electrocardiogram or removing baseline wander from the electrocardiogram.

9. The method of claim 7, wherein processing the raw data that characterizes the electrocardiogram of the patient comprises using a signal averaging technique to determine a representative beat of the electrocardiogram based on data that characterizes multiple beats of the patient.

10. The method of claim 7, wherein processing the raw data that characterizes the electrocardiogram of the patient comprises:
identifying one or more beats that are deemed outliers from one or more other beats represented in the electrocardiogram; and
generating a representative beat of the electrocardiogram based on data that characterizes a plurality of beats represented in the electrocardiogram to the exclusion of the one or more beats that are deemed outliers,
wherein the computing system performs at least one of the analyzing step or the determining step with respect to data that characterizes the representative beat.

11. The method of claim 7, wherein processing the raw data that characterizes the electrocardiogram of the patient comprises:
identifying data recorded from one or more leads of a multi-lead electrocardiogram device; and
removing the data recorded from the one or more leads of the multi-lead electrocardiogram device,
wherein the computing system performs at least one of the analyzing step or the determining step based on a portion of data received by the computing system that excludes the data recorded from the one or more leads of the multi-lead electrocardiogram device.

12. The method of claim 1, further comprising:
determining respective values of the one or more-features of the T-wave for a population of patients;
performing statistical analysis of the respective values of the one or more features of the T-wave for the population of patients; and
based on a result of the statistical analysis, correlating values of at least one feature of the T-wave with a patient condition.

13. The method of claim 12, comprising:
based on the result of the statistical analysis, correlating first values of at least one feature of the T-wave with congenital long-QT syndrome; and
based on the result of the statistical analysis, correlating second values of at least one feature of the T-wave with acquired long-QT syndrome.

14. The method of claim 1, wherein the one or more features of the T-wave comprise a slope of the T-wave in lead V6, wherein the prediction of the patient's risk of experiencing a future LQTS-associated cardiac event is determined based on the slope of the T-wave in lead V6.

15. The method of claim 1, wherein the one or more features of the T-wave comprise a center of gravity of the T-wave in the x-axis in lead I, wherein the prediction of the patient's risk of experiencing a future LQTS-associated cardiac event is determined based on the center of gravity of the T-wave in the x-axis in lead I.

16. The method of claim 1, wherein the LQTS-associated cardiac event comprises an LQTS-associated arrhythmia event.

17. The method of claim 1, comprising administering a treatment to the patient, the treatment being based on the prediction of the patient's risk of experiencing the future LQTS-associated cardiac event.

18. The method of claim 17, wherein administering the treatment comprises treating the patient with a beta blocker therapy, performing left cardiac sympathetic denervation (LCSD), or implanting a cardioverter defibrillator in the patient.

19. A method, comprising:
receiving, by a computing system, a set of data that characterizes an electrocardiogram of a patient having abnormal QT prolongation;
analyzing, by the computing system, the set of data that characterizes the electrocardiogram of the patient to identify a T-wave that occurs in the electrocardiogram;
determining, by the computing system and in response to identifying a T-wave that occurs in the electrocardiogram, values of one or more features of the T-wave, wherein the one or more features of the T-wave comprise at least one of T-wave left slope or T-wave center of gravity; and
determining, based on the values of the one or more features of the T-wave, a prediction of the patient's risk of experiencing a future long QT-syndrome (LQTS) associated cardiac event, wherein a treatment is administered to the patient based on the prediction.

20. The method of claim 19, wherein the one or more features of the T-wave comprise a slope of the T-wave in lead V6, wherein the prediction of the patient's risk of experiencing a future LQTS-associated cardiac event is determined based on the slope of the T-wave in lead V6.

21. The method of claim 19, wherein the one or more features of the T-wave comprise a center of gravity of the T-wave in the x-axis in lead I, wherein the prediction of the patient's risk of experiencing a future LQTS-associated cardiac event is determined based on the center of gravity of the T-wave in the x-axis in lead I.

22. The method of claim 19, wherein the treatment administered to the patient comprises a beta blocker therapy, a left cardiac sympathetic denervation (LCSD), or an implantation of a cardioverter defibrillator in the patient.

* * * * *

UNITED STATES PATENT AND TRADEMARK OFFICE
CERTIFICATE OF CORRECTION

PATENT NO. : 11,337,637 B2
APPLICATION NO. : 16/329480
DATED : May 24, 2022
INVENTOR(S) : Noseworthy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 118 days.

Signed and Sealed this
Fifteenth Day of November, 2022

Katherine Kelly Vidal
*Director of the United States Patent and Trademark Office*